United States Patent [19]
Morita

[11] Patent Number: 6,088,154
[45] Date of Patent: Jul. 11, 2000

[54] OPERATING MICROSCOPE

[75] Inventor: Kazuo Morita, Hachioji, Japan

[73] Assignee: Olympus Optical Co., Ltd., Tokyo, Japan

[21] Appl. No.: 09/053,620

[22] Filed: Apr. 2, 1998

[30]     Foreign Application Priority Data

| Apr. 3, 1997 | [JP] | Japan | 9-085286 |
| Dec. 22, 1997 | [JP] | Japan | 9-353354 |

[51] Int. Cl.[7] ................................................ G02B 21/22
[52] U.S. Cl. ......................... 359/375; 359/368; 359/630
[58] Field of Search .................................. 359/362–363, 359/368–369, 372–375, 380–383, 618, 629–630; 351/205–218; 600/166, 398; 606/3–4, 11, 18

[56]           References Cited

U.S. PATENT DOCUMENTS

| 5,042,930 | 8/1991 | Hutt | 359/375 |
| 5,095,887 | 3/1992 | Leon et al. | 600/166 |
| 5,295,477 | 3/1994 | Janfaza | 606/4 |
| 5,557,453 | 9/1996 | Schalz et al. | 359/368 |
| 5,601,549 | 2/1997 | Miyagi | 606/4 |
| 5,886,822 | 3/1999 | Spitzer | 359/630 |

FOREIGN PATENT DOCUMENTS 62-166310  7/1987  Japan .

*Primary Examiner*—Thong Nguyen
*Attorney, Agent, or Firm*—Pillsbury Madison & Sutro LLP

[57]           ABSTRACT

An operating microscope having an image projecting optical system (9) for introducing an image derived from an endoscopic optical system, which is provided separate from an operating-microscopic optical system, into an eyepiece optical system (18) of the operating microscope so that the operating-microscopic image and the endoscopic image can be simultaneously observed. The image projecting optical system (9) includes a collimating optical system (10), which collimates a beam of rays emergent from the image derived from the endoscopic optical system, and an imaging optical system (13), which forms an image on an image surface of the operating-microscopic optical system provided for observation via eyepiece using the beam of parallel rays emergent from the collimating optical system (10). The imaging optical system (13) is constructed to be movable at least in such a range that its entrance aperture can receive the beam of parallel rays. Whereby, the operating-microscopic image and the endoscopic images are simultaneously observed via the eyepiece optical system (18) of the operating microscope irrespective of adjustment of interpupillary distance, and the operating microscope is constructed to be compact and highly operable.

15 Claims, 19 Drawing Sheets

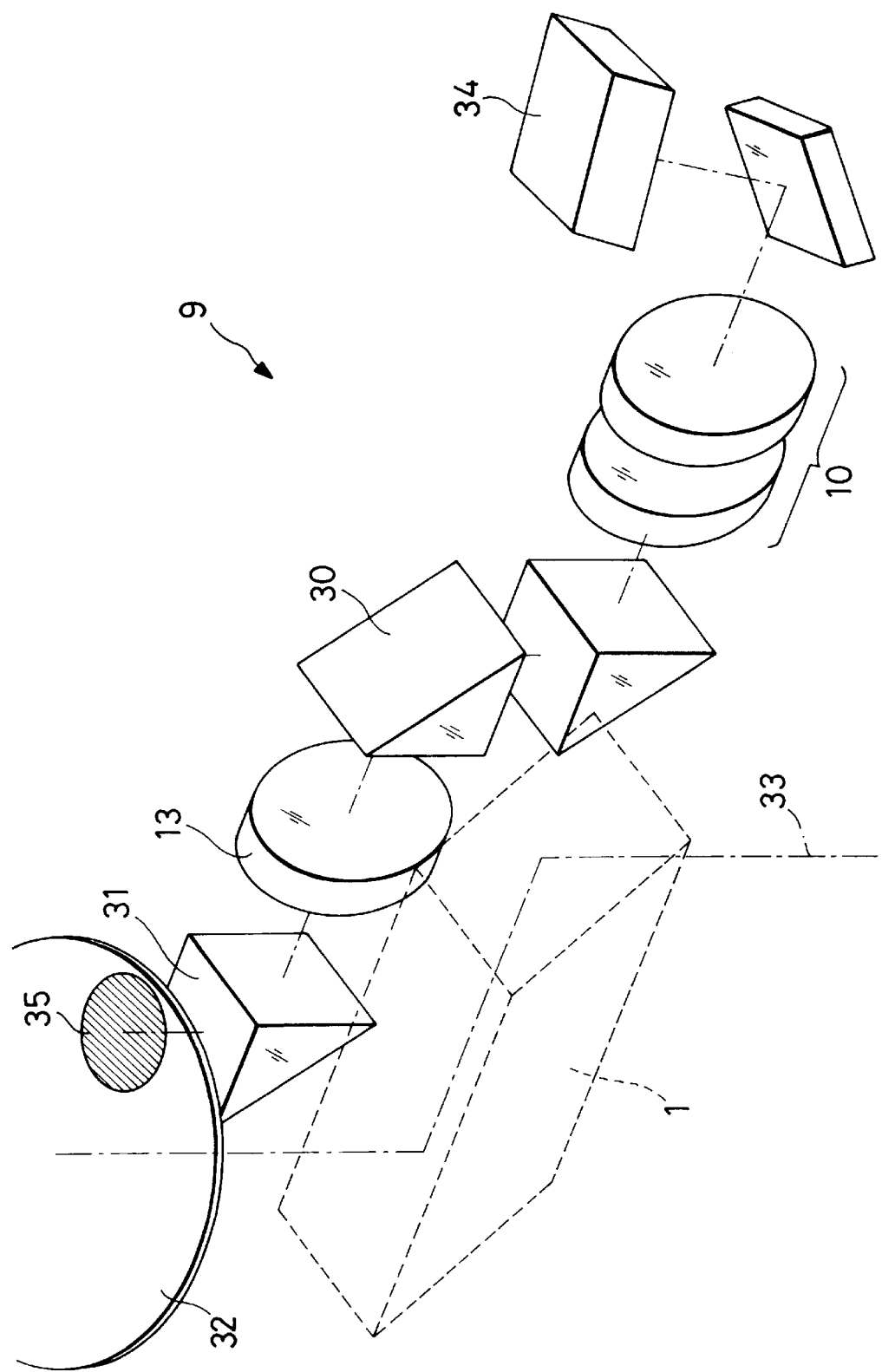

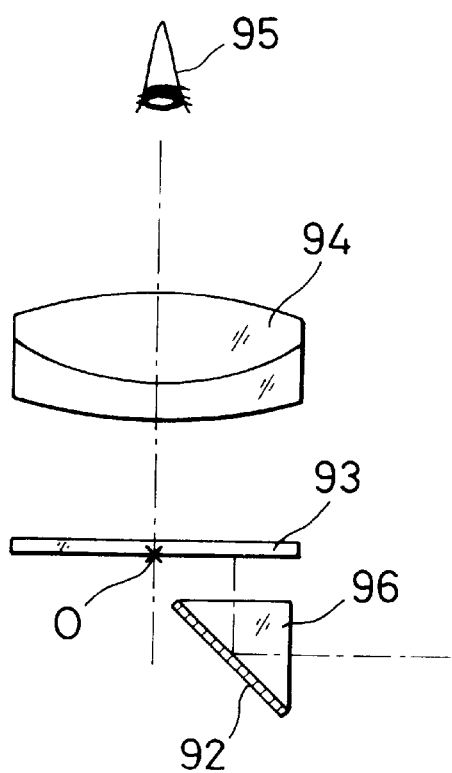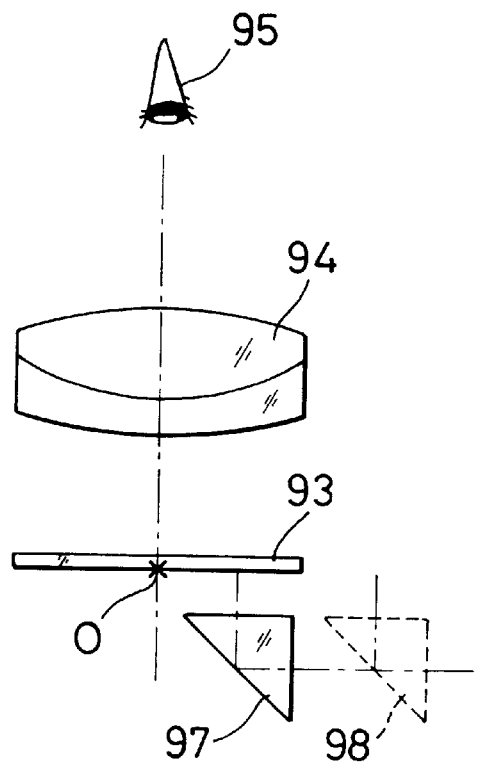

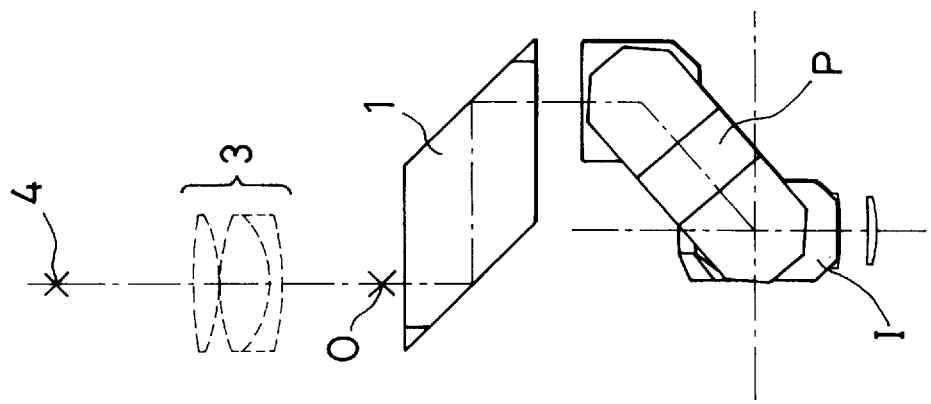
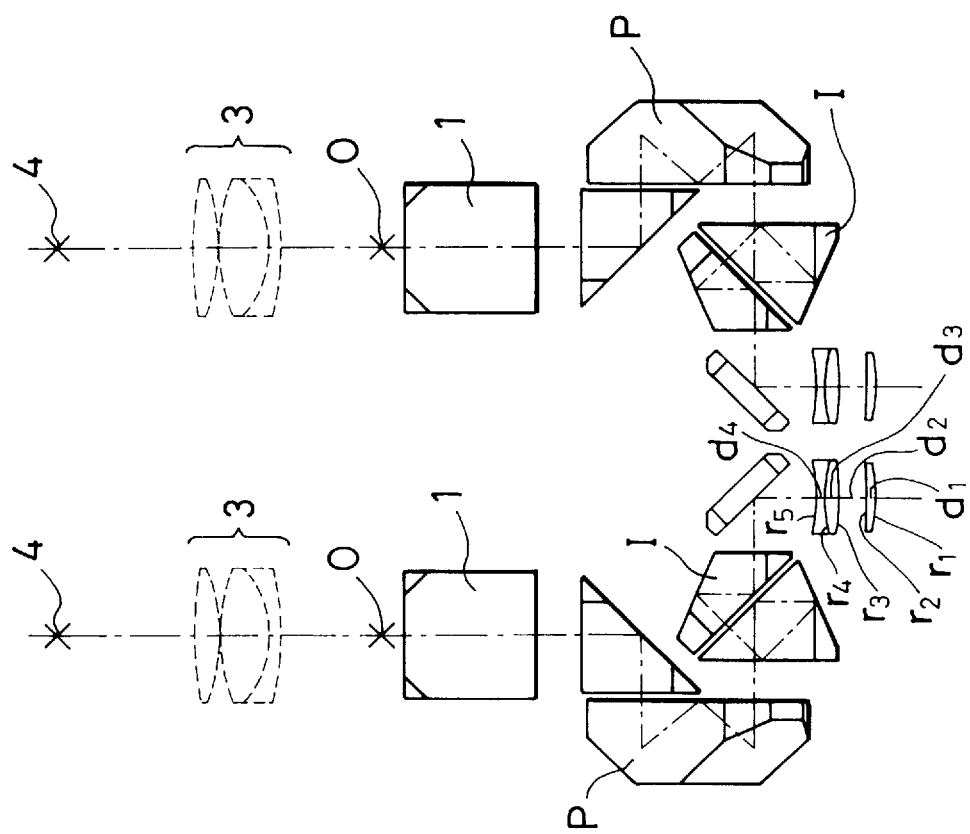
FIG. 20A
FIG. 20B

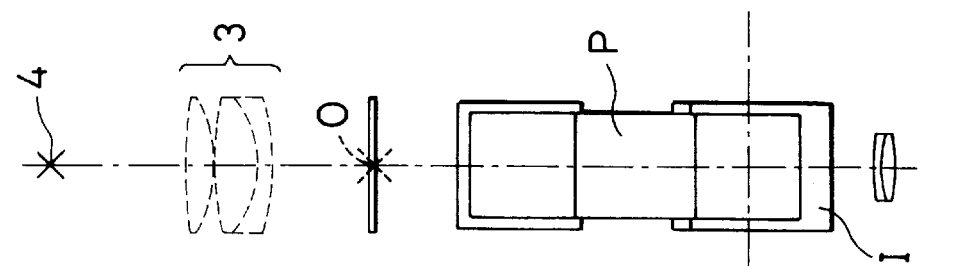
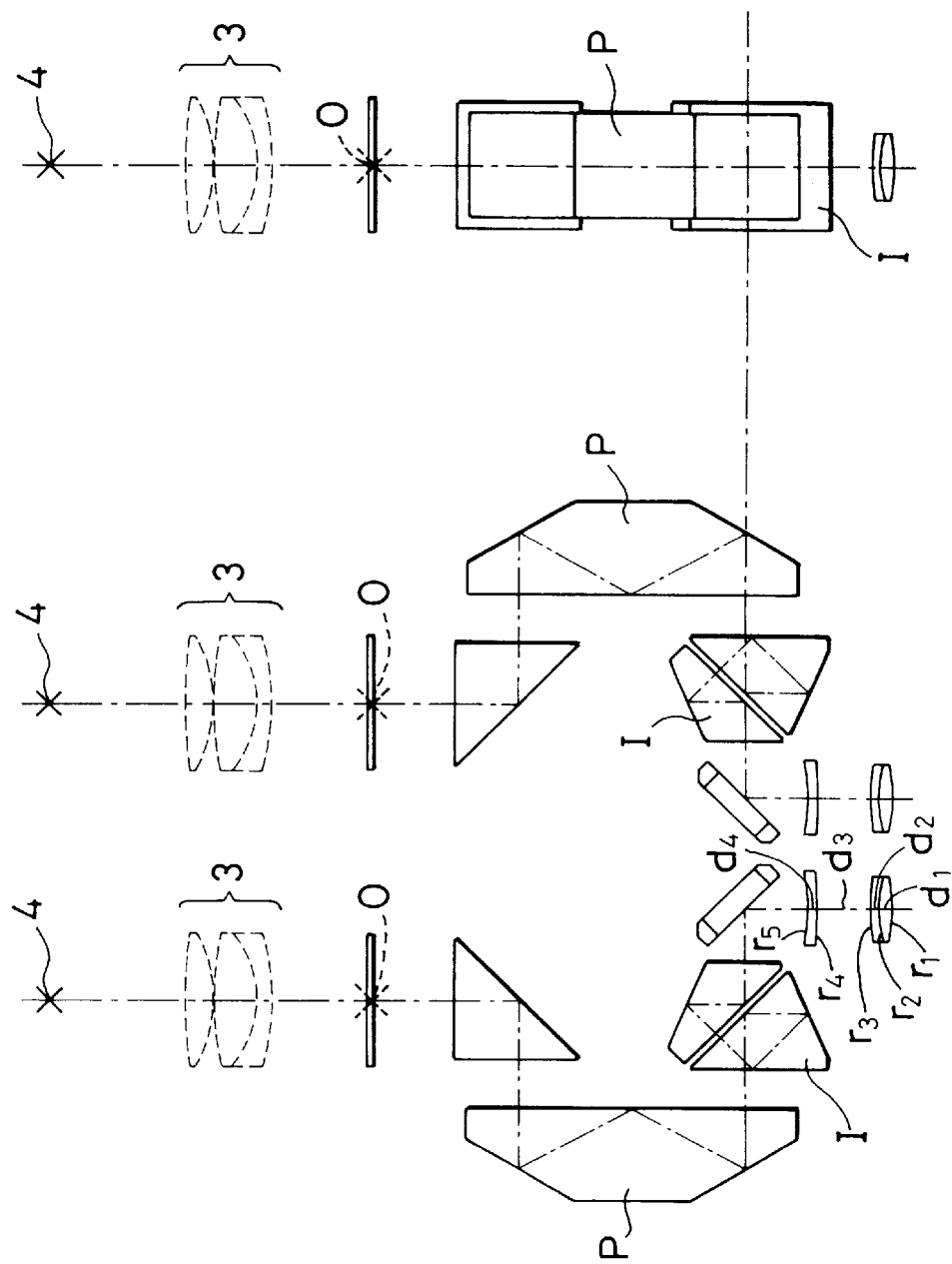

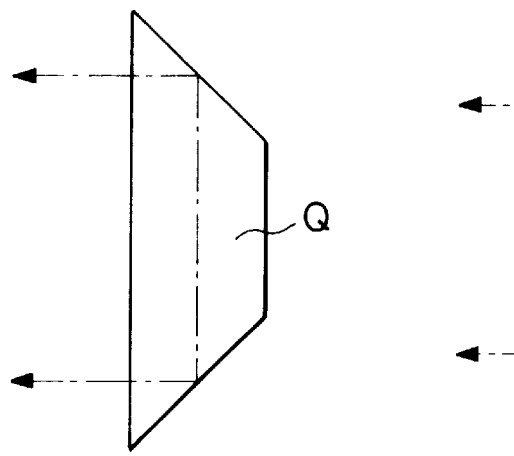
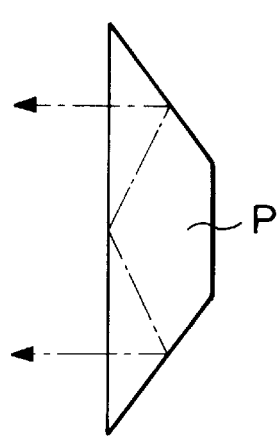
FIG. 22A  FIG. 22B
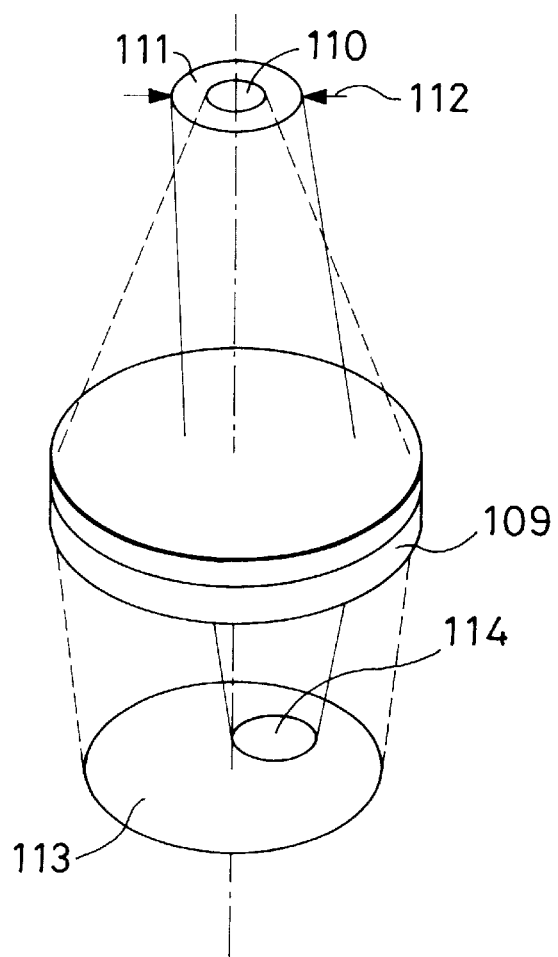
FIG. 23

OPERATING MICROSCOPE

BACKGROUND OF THE INVENTION a) Field of the Invention

This invention relates to an operating microscope, specifically to that incorporating an endoscopic image into an operating-microscopic image to allow simultaneous observation.

b) Description of the Related Art

For surgical treatment in cerebral neurosurgery, otorhinolaryngology, ophthalmology or other clinical specialty, operating microscopes have played such an important role as to improve efficiency of surgical operations by providing observers with enlarged images of parts subjected to the operations. Furthermore, in recent years, endoscopic observation also is applied to the operations that used to be performed only under the operating-microscopic observation, so that tissues other than the minimum necessary portions for the operation remain intact; it is preferred that the operating-microscopic image and the endoscopic image can be observed simultaneously.

A microscope apparatus disclosed by Japanese Patent Application Laid-Open Number Sho 62-166310, for example, is known to be directed to the combination of the operating microscope and the endoscope. In this apparatus, an endoscope with a solid-state image pickup device for stereoscopic observation is provided to be movable with respect to a stereoscopic microscope so as to allow observation inside a narrow cavity, which were impossible otherwise. Moreover, the apparatus includes an image reproducing means for displaying the image derived from the solid-state image pickup device and an image projecting means for introducing the image displayed on the image reproducing means into an eyepiece optical system so that the eyepiece optical system is commonly used for simultaneous observation of the operating-microscopic image and the endoscopic image.

However, the art of the Japanese Patent Application Laid-Open Number Sho 62-166310 fails to consider the problem caused by the shift of the image surfaces which are provided for observation via eyepiece, which shift accompanies adjustment of interpupillary distance, and thus cannot be reduced into realization for apractical operating microscope.

The adjustment of interpupillary distance is performed by shifting the left and right sections of the operating microscope, in each of which an image surface is provided for observation via eyepiece, so that the distance between the left and right eyepoints of the operating microscope corresponds to the distance between the left and right pupils of an observer. Every operating microscope is provided with a mechanism to perform this adjustment. If the interpupillary distance is to be adjusted in practice using only the art known from the above-mentioned Sho 62-166310, it is necessary to shift the image reproducing means through the image projecting means integral with the shift of the image surfaces provided for observation via eyepiece so that the positions on which the images from the image reproducing means are projected follow movement of the eyepiece optical system resulting from the adjustment of interpupillary distance. This configuration requires a space for movement of optical system or elements inside a housing of the operating microscope, to render the housing voluminous. As a result, according to the art of the above-mentioned Sho 62-166310, it is impossible to make an operating microscope compact in its entirety, while the operating microscope is fundamentally required to be made compact for efficiency of the surgical work.

SUMMARY OF THE INVENTION

The present invention is made considering the above-mentioned problem of the conventional art. An object of the present invention is to provide an operating microscope in which the operating-microscopic image and the endoscopic image can be constantly and simultaneously observed via the eyepiece optical system irrespective of adjustment of interpupillary distance by causing images obtained from an endoscopic optical system to be projected as to follow the shift of the image surfaces of the operating-microscopic optical system resulting from the adjustment of interpupillary distance, and which is also made compact to facilitate the surgical work.

In order to attain the above-mentioned object, according to the present invention, an operating microscope comprising an image projecting optical system for introducing an image derived from an endoscopic optical system, which is provided separate from an operating-microscopic optical system, into an eyepiece optical system of the operating microscope so that the operating-microscopic image and the endoscopic image can be simultaneously observed is characterized; in that the image projecting optical system includes a collimating optical system, which collimates a beam of rays emergent from the image derived from the endoscopic optical system, and an imaging optical system, which forms an image on an image surface of the operating-microscopic optical system provided for observation via eyepiece using the beam of parallel rays emergent from the collimating optical system; and in that the imaging optical system is constructed to be movable at least in such a range that its entrance aperture can receive the beam of parallel rays.

According to this configuration, an image by the endoscopic optical system can be projected on the image surface as to follow the same, which is constructed to be movable for adjustment of interpupillary distance. Therefore, the observer can observe the operating-microscopic image and the endoscopic image constantly and simultaneously, irrespective of the adjustment of interpupillary distance.

Furthermore, since the collimating optical system is fixedly placed during the adjustment of interpupillary distance of the operating microscope, a space for moving the collimating optical system therein is not necessary in a housing of the operating microscope, which feature facilitates compact design of the operating microscope.

Furthermore, the image projecting optical system and the operating-microscopic optical system are provided independent of each other, without any common constituent optical element. Therefore, these optical systems do not degrade images formed by each other, and thus both the images can be viewed clearly.

Also, according to the present invention, an operating microscope comprising an image projecting optical system for introducing images derived from an endoscopic optical system, which is provided separate from an operating-microscopic optical system, into an eyepiece optical system of the operating microscope so that the operating-microscopic image and the endoscopic image can be simultaneously observed is characterized; in that the image projecting optical system includes a collimating optical system, which collimates a beam of rays emergent from the image by the endoscopic optical system, and an imaging optical system, which forms an image onto an image surface of the operating-microscopic optical system using the beam of parallel rays emergent from the collimating optical system; and in that an optical axis of the imaging optical system aligned with the beam of parallel rays is parallel to a direction in which the eyepiece optical system, onto which the image by the endoscopic optical system is projected, slides for adjustment of interpupillary distance as well as the imaging optical system is constructed to be movable along the optical axis in such a range that its entrance aperture can receive the beam of parallel rays.

The image projecting optical system of this configuration is preferably applicable to an operating microscope provided with a Jentzsche system for adjustment of interpupillary distance. According to this configuration, an image by the endoscopic optical system can be projected on the image surface as to follow the same, which is constructed to be slidable for the adjustment of interpupillary distance. Therefore, the observer can observe the operating-microscopic image and the endoscopic image constantly and simultaneously, irrespective of the adjustment of interpupillary distance.

Furthermore, since the collimating optical system is fixedly placed during the adjustment of interpupillary distance of the operating microscope, a space for moving the collimating optical system therein is not necessary in a housing of the operating microscope, which feature facilitates compact design of the operating microscope.

Furthermore, the image projecting optical system and the operating-microscopic optical system are provided independent of each other, without any common constituent optical element. Therefore, these optical systems do not degrade images formed by each other, and thus both the images can be viewed clearly.

Also, according to the present invention, an operating microscope comprising an image projecting optical system for introducing an image derived from an endoscopic optical system, which is provided separate from an operating-microscopic optical system, into an eyepiece optical system of the operating microscope so that the operating-microscopic image and the endoscopic image can be simultaneously observed is characterized; in that the image projecting optical system includes a collimating optical system, which collimates a beam of rays emergent from the image by the endoscopic optical system, and an imaging optical system, which forms an image onto am image surface of the operating-microscopic optical system using the beam of parallel rays emergent from the collimating optical system; and in that an optical axis of the imaging optical system aligned with the beam of parallel rays is perpendicular to a direction in which the eyepiece optical system, onto which the image by the endoscopic optical system is projected, slides for adjustment of interpupillary distance as well as the imaging optical system is constructed to be movable in a plane perpendicular to the beam of parallel rays in such a range that its entrance aperture can receive the beam of parallel rays.

The image projecting optical system of this configuration is preferably applicable to an operating microscope provided with a Siedentoph system for adjustment of interpupillary distance. According to this configuration, an image by the endoscopic optical system can be projected on the image surface as to follow the same, which is constructed to be slidable for the adjustment of interpupillary distance. Therefore, the observer can observe the operating-microscopic image and the endoscopic image constantly and simultaneously, irrespective of the adjustment of interpupillary distance.

Furthermore, since the collimating optical system is fixedly placed during the adjustment of interpupillary distance of the operating microscope, a space for moving the collimating optical system therein is not necessary in a housing of the operating microscope, which feature facilitates compact design of the operating microscope.

Furthermore, the image projecting optical system and the operating-microscopic optical system are provided independent of each other, without any common constituent optical element. Therefore, these optical systems do not degrade images formed by each other, and thus both the images can be viewed clearly.

Also, according to the present invention, an operating microscope comprising an image projecting optical system for introducing an image derived from an endoscopic optical system, which is provided separate from an operating-microscopic optical system, into an eyepiece optical system of the operating microscope so that the operating-microscopic image and the endoscopic image can be simultaneously observed is characterized in that at least one pair of trapezoidal prisms are arranged in mirror symmetry in a binocular optical system of the entire operating-microscopic optical system to act as path deflecting means by reflecting rays three times inside themselves.

In order to achieve compact design of an operating microscope provided with an image projecting optical system, not only the image projecting optical system but also the operating-microscopic optical system are required to be compact. The above-mentioned configuration using the three-times reflection prisms is advantageous for its compactness in thickness direction over a configuration in which trapezoidal prisms are arranged to reflect rays twice inside themselves as the path deflecting means (FIG. 20A). Therefore, the above-mentioned configuration of the present invention is capable of providing an operating microscope that is small in size but allows simultaneous observation of operating-microscopic image and endoscopic image, by reducing thickness of the binocular optical system of the entire operating-microscopic optical system, which is to be juxtaposed with the image projecting optical system.

In describing the invention, the present inventor often uses the terms "Jentzsche" and "Siedentoph" to divide adjustment systems for interpupillary distance into two types. This classification is made not by the structure of the adjustment device but by how the binocular eyepiece moves. Those adjusting interpupillary distance by shifting the left and right eyepieces linearly along a single line are referred to as Jentzsche type system, while those adjusting interpupillary distance by moving the left and right eyepieces along an arcuate locus are referred to as Siedentoph type system.

This and other objects as well as the features and advantages of the present invention will become apparent from the following detailed description of the preferred embodiments when taken in conjunction with the accompanying drawings.

BRIEF DESCRIPTION OF THE DRAWINGS

FIG. 4 is an explanatory view illustrating how rays are reflected by prisms and mirrors of an image projecting optical system used in the first embodiment;

FIG. 15 is directed to the third embodiment of the present invention, showing that a light intercepting member is disposed in the movable section of such an image projecting optical system as used in the first or second embodiment;

FIG. 16 is directed to the fourth embodiment of the present invention, showing that a movable prism is arranged in the movable section of such an image projecting optical system as used in the first or second embodiment;

FIG. 20A is a plan view directed to the eighth embodiment of the present invention, showing arrangement of the binocular optical system of the entire operating-microscopic optical system, where Siedentoph system is incorporated to adjust interpupillary distance;

FIG. 20B is a side view of FIG. 20A;

FIG. 21A is a plan view directed to the eighth embodiment of the present invention, showing arrangement of the binocular optical system of the entire operating-microscopic optical system, where Jentzsche system is incorporated to adjust interpupillary distance;

FIG. 21B is a side view of FIG. 21A;

FIG. 22A illustrates how rays are reflected by a trapezoidal prism of one example that is applicable to the binocular optical system;

FIG. 22B illustrates how rays are reflected by a trapezoidal prism used in the binocular optical system according to the eighth embodiment;

FIG. 23 illustrates pupil arrangement in detail about the eyepiece optical system according to the ninth embodiment of the present invention;

DETAILED DESCRIPTION OF THE PREFERRED EMBODIMENTS

First Embodiment

In reference to FIGS. 1 and 2, description will be made of the configuration of optical systems in the binocular section of an operating microscope according to the first embodiment of the present invention.

Figure 1:
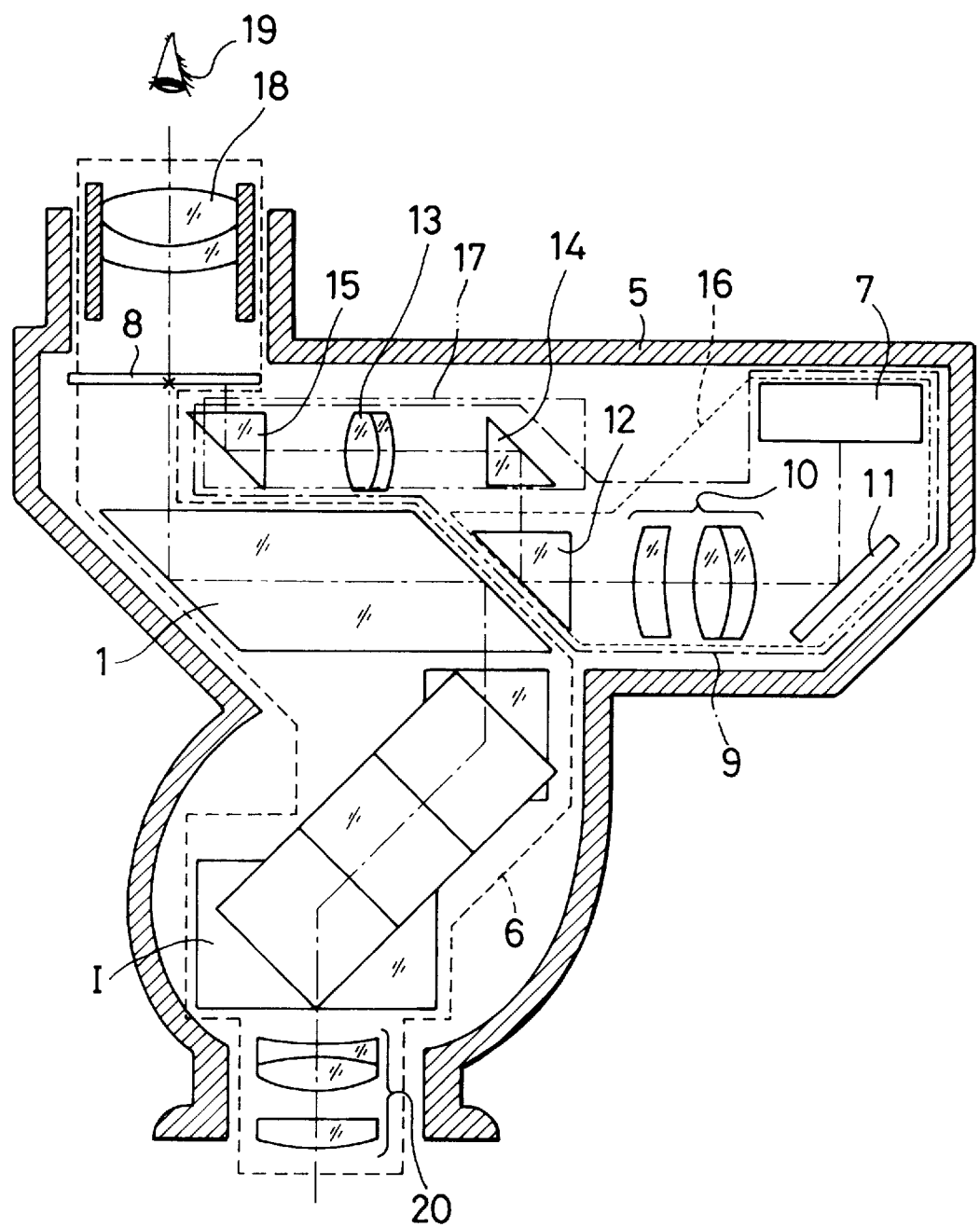
FIG. 1 is a right-side sectional view of optical systems in a binocular section of the operating microscope according to the first embodiment of the present invention, for showing the overall configuration of the optical systems.
Figure 2:
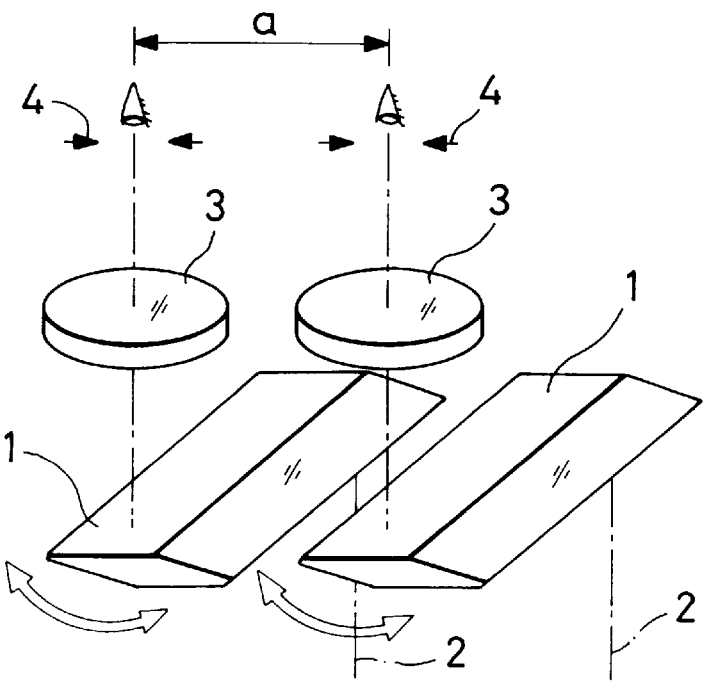
FIG. 2 is an explanatory view illustrating the eyepiece optical system shown in FIG. 1.

As shown in FIG. 1, optical components housed in a binocular housing 5 is roughly divided into a binocular optical system 6 of the entire operating-microscopic optical system and an image projecting optical system 9 for introducing light emergent from a compact LCD 7 into a right image surface 8 of the binocular optical system 6.

Although FIG. 1 shows only the right-side optical members of the binocular optical system 6, the first embodiment is provided with left-side optical members of identical structure as a matter of course. The binocular optical system 6 of the entire operating-microscopic optical system includes, on each of left and right sides, an imaging optical system 20, an image rotator I, a parallelogram prism 1, an image surface 8 provided for observation via eyepiece, and an eyepiece optical system 18. The binocular optical system 6 employs Siedentoph method for adjusting interpupillary distance; as illustrated in FIG. 2, the parallelogram prisms 1 pivot on center axes 2 of beams of rays incident thereon integral with the respective eyepiece optical systems 3 disposed on the exit side thereof so as to adjust distance "a" between left and right eyepoints 4.

The image projecting optical system 9 includes a compact LCD 7 on which an electronic image is displayed, a mirror 11, a collimating optical system 10 for collimating a beam of rays emergent from the LCD 7, a prism 12, an imaging optical system 13 for forming an image onto the right image surface 8 using a beam of parallel rays emergent from the collimating optical system 10, and prisms 14 and 15. The collimating optical system 10, the compact LCD 7, the mirror 11, and the prism 12 constitute a fixed section 16, which remains stationary during the adjustment of interpupillary distance of the binocular eyepiece, while the imaging optical system 13 and prisms 14 and 15 constitute a movable section 17, which moves integral with the right image surface 8 in accordance with the adjustment of interpupillary distance of the binocular eyepiece of the operating microscope.

The light beam travelling between the fixed section 16 and the movable section 17 in the image projecting optical system 9 is constructed of parallel rays. Therefore, even if the movable section 17 shifts in accordance with the adjustment of interpupillary distance of the binocular eyepiece of the operating microscope, the electronic image from the compact LCD 7 can always be projected onto the image surface 8 as long as the shift is made within such a range as allows the entrance aperture of the movable section 17 to receive the beam of parallel rays. Accordingly, the observer, whose pupil 19 is set behind the eyepiece optical system 18, can view the electronic image from the compact LCD 7 inside an observation field formed by the right eyepiece optical system 18 of the operating-microscopic optical system.

Next, the optical principle relating to the image projecting optical system with the above-mentioned configuration of the first embodiment will be described in reference to FIGS. 3A and 3B. According to FIGS. 3A and 3B, the compact LCD is represented by the reference numeral 21, the beam of rays emergent from the compact LCD 21 by the reference numeral 22, the fixed section of the image projecting optical system by the reference numeral 23, the collimating optical system by the reference numeral 24, the beam of parallel rays by the reference numeral 25, the movable section of the image projecting optical system by the reference numeral 26, the center axis of the beam of parallel rays 25 by the reference numeral 27, the image surface provided for observation via eyepiece by the reference numeral 28, and the imaging optical system by the reference numeral 29.

Figure 3A:
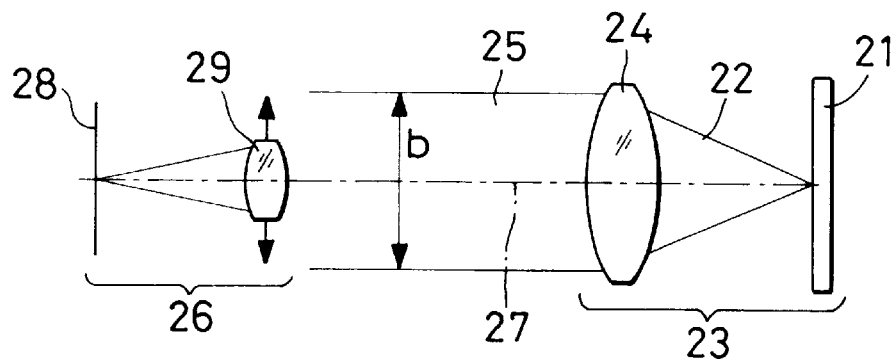
FIG. 3A is a view for explaining the optical principle of the first embodiment shown in FIG. 1, illustrating a condition where an imaging optical system is disposed in the center axis of a beam of parallel rays.
Figure 3B:
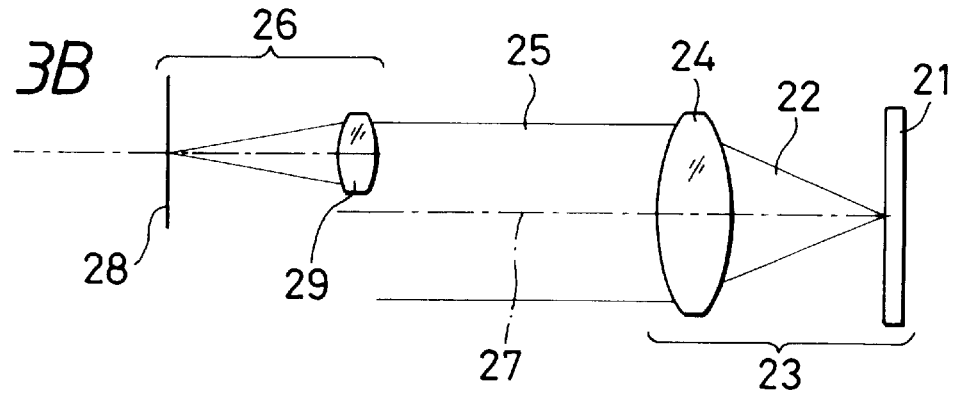
FIG. 3B is a view for explaining the optical principle of the first embodiment, illustrating a condition where the imaging optical system is shifted from the center axis in a plane perpendicular to the beam of parallel rays.

As shown in FIG. 3A, the beam of rays 22 emergent from the compact LCD 22 is transmitted through the collimating optical system 24 to become the beam of parallel rays 25. Since each of optical elements constituting the fixed section 23 has such a large diameater as to cover the moving range of the movable section 26, of the beam of parallel rays 25 with a large breadth (diameater) "b" also covers the moving range of the movable section 26. As a result, as shown in FIG. 3B, the imaging optical system 29 can always receive the beam from the compact LCD 21 in the constant condition even if it shifts along a plane perpendicular to the center axis 27 of the beam of parallel rays 25. Furthermore, since the image surface 28 shifts integral with the imaging optical system 29, the imaging optical system 29 constantly forms an image derived from the electronic image on a predetermined position on the image surface 28.

Next, in reference to FIG. 4, it will be explained how a beam of light rays is reflected by prisms and mirrors of the image projecting optical system used in the first embodiment. According to FIG. 4, the prisms are represented by the reference numerals 30 and 31, the image surface provided for observation via eyepiece by the reference numeral 32, the center axis of the beam of rays incident on the parallelogram prism 1 by the reference numeral 33, the compact LCD by the reference numeral 34, and a projected image by the reference numeral 35.

As shown in FIG. 4, the two prisms 30 and 31 included in the movable section of the image projecting optical system 9 are so arranged as to direct the beam emergent from the fixed section of the image projecting optical system 9 toward the image surface 32 by reflecting it twice without changing travelling direction of the beam. According to this configuration, even if the movable section of the image projecting optical system 9 pivots on the center axis 33 of the beam incident on the parallelogram prism 1 integral with the parallelogram prism 1, the projected image 35 derived from the electronic image on the compact LCD 34 do not rotate; the electronic image displayed on the compact LCD 34 is constantly projected in its proper attitude onto the image surface 32.

Next, description will be made of an application where the operating microscope with the above-mentioned structure is used with an endoscope provided with CCD in reference to FIG. 5. According to this application, an endoscope 37 with a CCD, a camera control unit 41, a light source unit 42 for the endoscope 37, a CCD camera adapter 43 for endoscopes, a binocular section 48 of the operating microscope, a main section 49 of the operating microscope, a light source unit 44 for the operating microscope, light guides 46 and 47, and a cable 45 are interconnected as schematically shown in FIG. 5.

Figure 5:
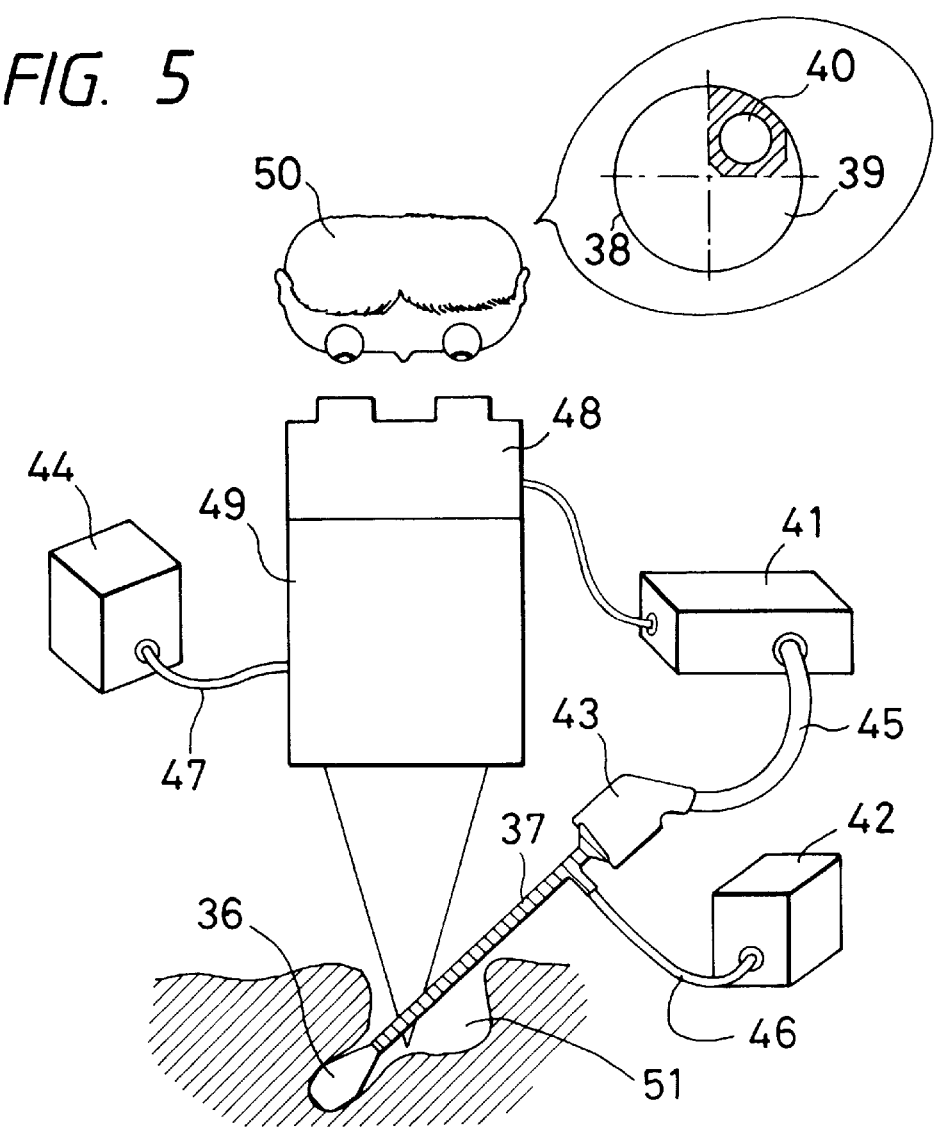
FIG. 5 is a schematic view showing an application where an endoscope provided with a CCD cooperates with the operating microscope illustrated in FIGS. 1 through 4.

As shown in FIG. 5, the endoscope 37 with a CCD cooperates with the operating microscope so as to facilitate observation of a narrow cavity interior 36 located in parts 51 under operation, which is not observable by the operating microscope alone. If an electronic image picked up by the endoscope 37 is displayed on the compact LCD 34 (FIG. 4) of the image projecting optical system 9 (FIGS. 1, 3 and 4), this electronic image displayed on the compact LCD 34 also is projected onto the right image surface as to follow the same, which is constructed to be movable for adjustment of interpupillary distance of the binocular section 48, and thereby an observer 50 can observe an operating-microscopic image 39 and an endoscopic image 40 simultaneously within an observation field 38 formed by the right eyepiece optical system.

In addition, according to the first embodiment, since the compact LCD 7, the collimating optical system 10, the mirror 11 and the prism 12, which occupy a considerable space in the binocular housing 5, are fixedly positioned as shown in FIG. 1, the housing 5 is not required to provide an extra space for their movement and accordingly, a compact operating microscope with high operability is realized while achieving the above-mentioned advantage, i.e. simultaneous observation of the operating-microscopic image and the endoscopic image.

Next, in reference to FIG. 6, description will be made of the image provided for observation via right eyepiece of the operating microscope according to the first embodiment. According to FIG. 6, the observation field formed by eyepiece of the operating microscope is represented by the reference numeral 52, the operating-microscopic image by the reference numeral 55, and the endoscopic image by the reference numeral 56.

The image projecting optical system 9 (FIGS. 1, 3 and 4) of the first embodiment projects the electronic image displayed on the compact LCD 34 (FIG. 4) onto the right image surface 8 (FIG. 1) so that the endoscopic image 56 is located at a peripheral portion 53 in the upper-right quadrant of the observation field 52. As a result, the vicinity of a field center 54 of the observation field 52 of the microscope is reserved for the operating-microscopic image 55.

According to this configuration, observation of the operating-microscopic image 55, which is the principal image, is compatible with observation of the endoscopic image 56, which serves as an auxiliary image. On the other hand, since an object located in the vicinity of the field center 54 is used as a target to be in focus by an auto-focusing device, it is necessary in using a microscope with auto-focusing function that the vicinity of the field center 54 is occupied by the operating-microscopic image 55. The image arrangement in the observation field according to the first embodiment is preferable also in that it would not affect auto-focus function.

According to the first embodiment, the electronic image displayed on the compact LCD 34 (FIG. 4) is projected onto the right image surface of the operating-microscope optical system. If it is projected onto the left image surface instead of the right image surface, the same effect can be obtained.

Figure 6:
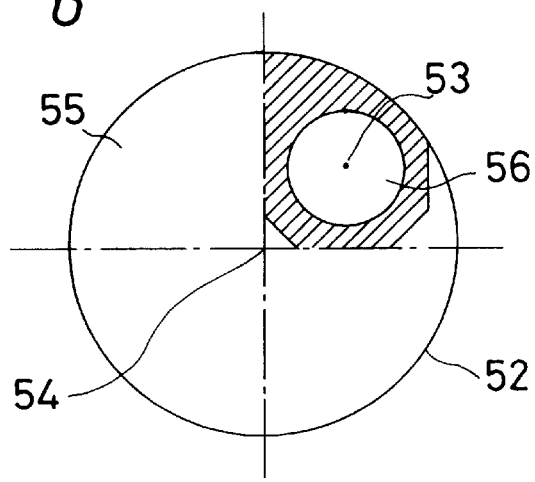
FIG. 6 shows an image obtained through the right eyepiece of the operating microscope according to the first embodiment.

Also, FIG. 6 shows that the electronic image appears at the peripheral portion in the upper-right quadrant of the observation field, it may be located on any other quadrant. For instance, the electronic image may be located, not limited to the upper-right quadrant, at a peripheral portion in the upper-left quadrant.

Also, the electronic image displayed on the compact LCD 34 (FIG. 4) is not necessarily limited to that obtained from the endoscope. An image derived from other image pickup optical system such as a video camera is applicable, or there may be directly displayed an electronically produced image such as a picture created by computer graphics or a waveform display obtained from a nerve monitor, which is indispensably used in certain operations.

Also, the compact LCD 34 (FIG. 4) used in the first embodiment may be replaced by other electronic image display means, such as a plasma display.

Figure 7:
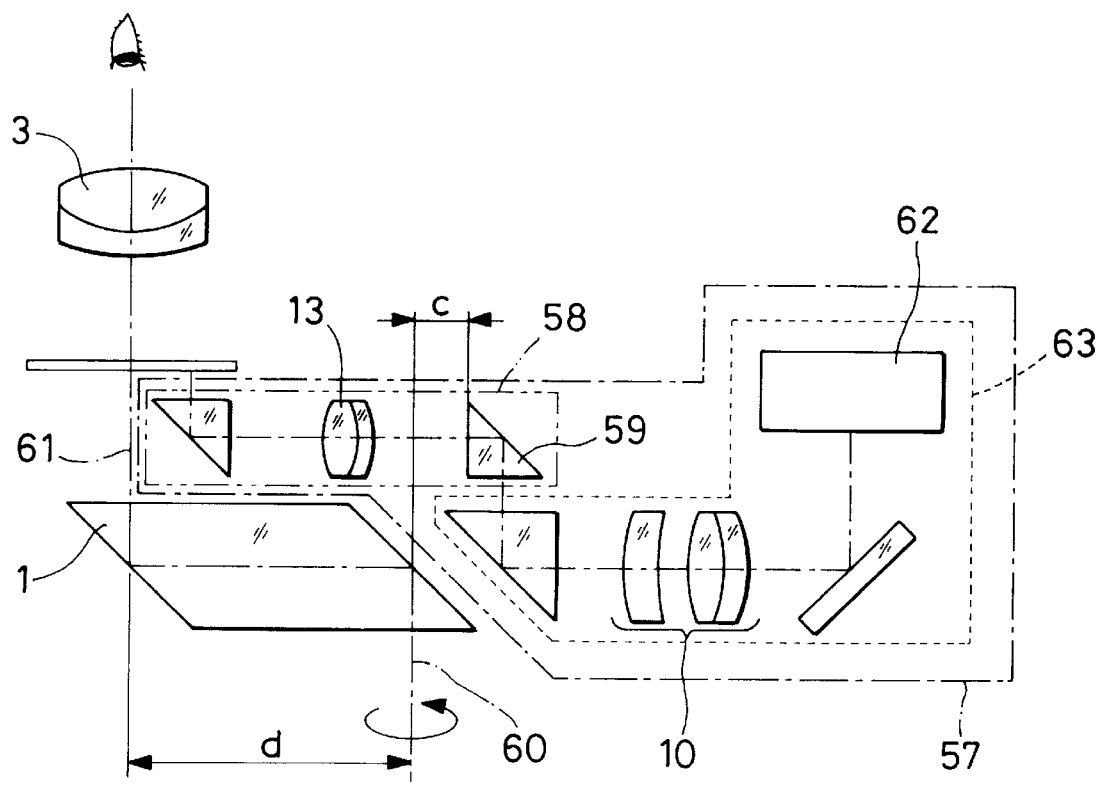
FIG. 7 is a side view of optical systems in the binocular section of the operating microscope according to the first embodiment, which is provided with a Siedentoph system for adjustment of interpupillary distance, selectively showing the movable units for interpupillary adjustment including the parallelogram prism, the eyepiece optical system and the image projecting optical system, to detail their configuration.

Next, in reference to FIG. 7, the configuration of the binocular section used in the first embodiment, which employs Siedentoph system for adjustment of interpupillary distance, will be detailed. According to FIG. 7, the image projecting optical system is represented by the reference numeral 57, the movable section of the image projecting optical system 57 by the reference numeral 58, the rotation axis of the parallelogram prism 1 by the reference numeral 60, the compact LCD by the reference numeral 62, and the fixed section of the image projecting optical system 57 by the reference numeral 63.

Of optical elements constituting the movable section 58, which moves in accordance with adjustment of interpupillary distance of the binocular eyepiece, an optical element 59, which is the first element to receive the beam emergent from the compact LCD 62, is disposed at a position separate from the rotation axis 60 of the parallelogram prism 1 by the distance c=20 mm. Also, arrangement is made so that an optical axis 61 of the eyepiece optical system 3 is separate from the rotation axis 60 of the parallelogram prism 1 by the distance d=34.5 mm.

According to this configuration, shift amount of the optical element 59 in accordance with the adjustment of interpupillary distance is smaller than that of the image surface. Consequently, the fixed section 63 of the image projecting optical system 57, which is designed to forward the beam from the compact LCD 62 to the movable section 58 as stationary positioned during the adjustment of interpupillary distance, can be made more compact. While arrangement is made so that c=20 mm according to the first embodiment, the distance "c" may be set at a value smaller than 20 mm.

Furthermore, the image projecting optical system 9 and the operating-microscopic optical system are provided independent of each other, without any common constituent optical element until the image surface. Therefore, these optical systems do not degrade images formed by each other, and thus both the images can be viewed clearly.

Second Embodiment

In reference to FIGS. 8, 9 and 10, description will be made of an optical arrangement around eyepiece optical systems and image projecting optical systems according to the second embodiment of the present invention.

Figure 8:
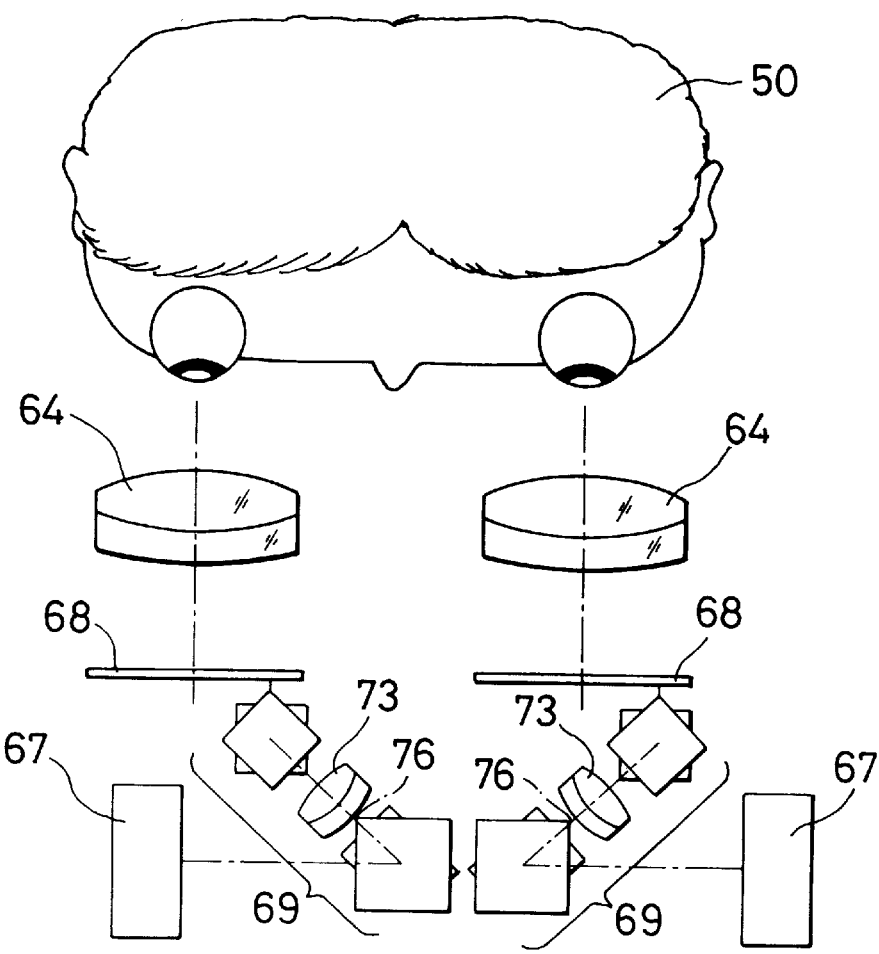
FIG. 8 is a front view of optical arrangement around the eyepiece optical system and the image projecting optical system according to the second embodiment of the present invention.
Figure 9:
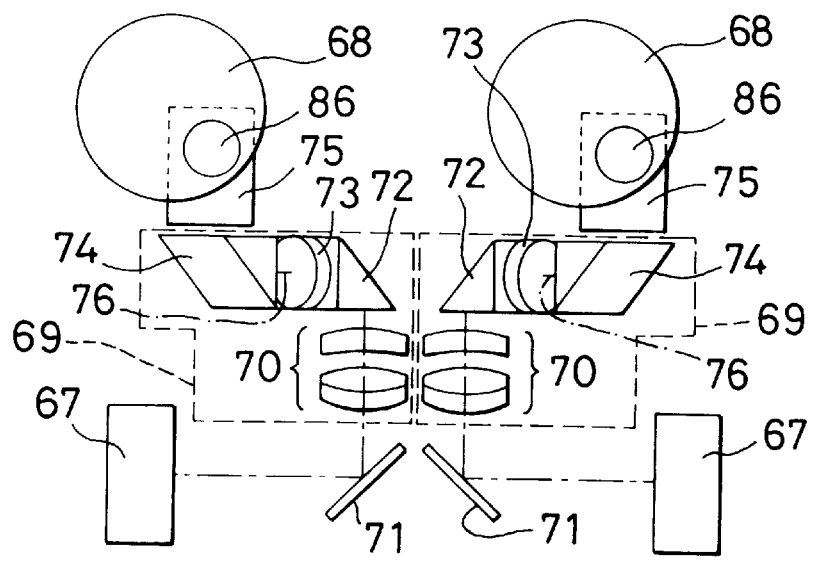
FIG. 9 is a plan view of the optical arrangement around the eyepiece optical system and the image projecting optical system according to the second embodiment of the present invention.
Figure 10:
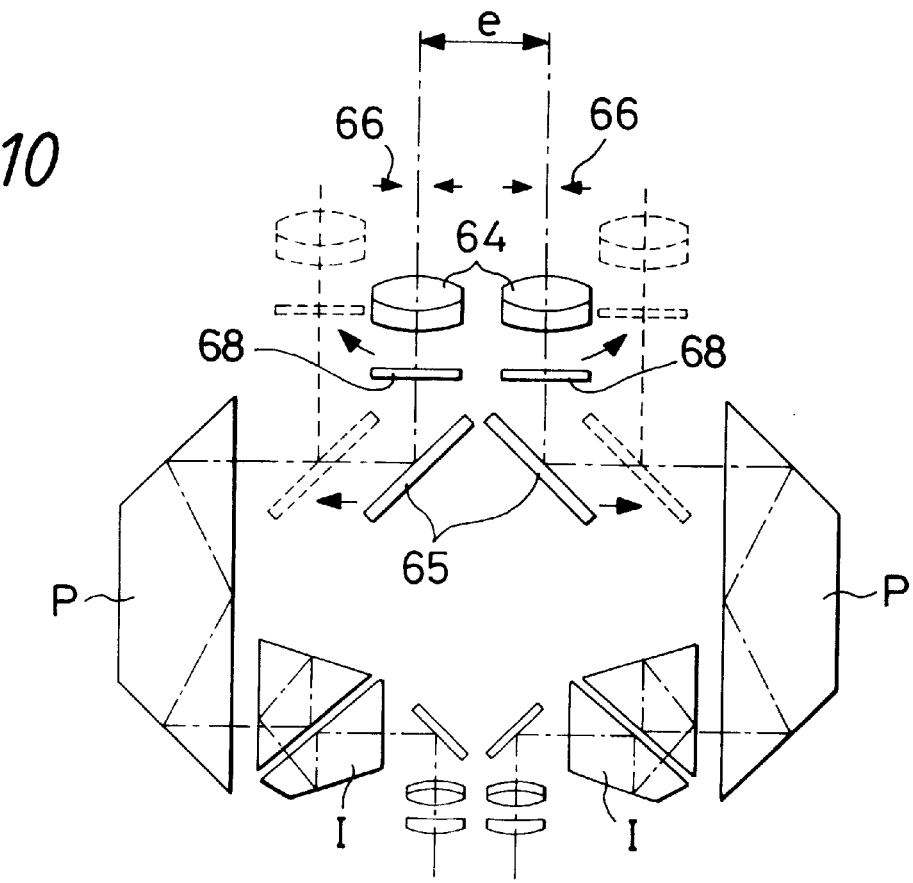
FIG. 10 shows the binocular optical system of the entire operating-microscopic optical system according to the second embodiment, to explain that this embodiment employs Jentzsche method for adjusting interpupillary distance of the binocular eyepiece.

According to the second embodiment, a binocular housing not shown in the drawings houses a binocular optical system (of the entire operating-microscopic optical system) shown in FIG. 10 and, as shown in FIGS. 8 and 9, a pair of compact LCDs 67 for displaying thereon electronic images and a pair of image projecting optical systems 69 for introducing light emergent from the compact LCDs 67 into left and right image surfaces 68 included in the binocular optical system of the entire operating-microscopic optical system.

According to the second embodiment, the binocular optical system of the entire operating-microscopic optical system employs Jentzsche system for adjusting interpupillary distance; as illustrated in FIG. 10, a pair of mirrors 65 disposed directly before a pair of eyepiece optical systems 64 slide in mutually opposite directions while the left and right eyepiece optical systems 64 slide in resultant directions of their respective horizontal components corresponding to the horizontal movement of the mirrors 65 and a vertical component for compensation for change of path length caused by the movement of the mirrors 65, so as to change distance "e" between left and right eyepoints 66. Although not described in detail here, the binocular optical system according to the second embodiment includes a pair of trapezoidal prisms P to reflect rays three times inside themselves, as shown in FIG. 10.

As shown in FIGS. 8 and 9, each of the image projecting optical systems 69 includes a collimating optical system 70 for collimating a beam of rays emergent from the LCD 67, a prism 72, an imaging optical system 73 for forming an image onto the image surface 68 using a beam of parallel rays emergent from the collimating optical system 70, and a prism 74. The collimating optical system 70, the compact LCD 67, a mirror 71, and the prism 72 constitute a fixed section, which remains stationary during the adjustment of interpupillary distance of the binocular eyepiece, while the imaging optical system 73 and prisms 74 and 75 constitute a movable section, which moves integral with the image surface 68 in accordance with the adjustment of interpupillary distance of the binocular eyepiece of the operating microscope.

The light beam travelling between the fixed section and the movable section in the image projecting optical system 69 is constructed of parallel rays. The prism 72 is located so that an optical axis 76 of the imaging optical system 73 aligned with a central axis of the beam of parallel rays runs parallel to the slide direction of the image surface 68, onto which the electronic image is projected. Also, the imaging optical system 73 and the prism 74 in the movable section are constructed to slide on the optical axis 76 integral with the image surface 68 in accordance with the adjustment of interpupillary distance so that the entrance aperture of the movable section also slides as inserted in the optical axis 76. Therefore, even if the movable section slides in accordance with the adjustment of interpupillary distance of the binocular eyepiece of the operating microscope, the electronic image from the compact LCD 67 can always be projected onto the image surface 68. Accordingly, as shown in FIG. 8, the observer 50 can view the electronic images from the compact LCDs 67 inside observation fields formed by the left and right eyepiece optical systems 64 of the operating-microscopic optical system.

Next, the optical principle relating to the image projecting optical system with the above-mentioned configuration of the second embodiment will be described in reference to FIGS. 11A and 11B. According to FIGS. 11A and 11B, the compact LCD is represented by the reference numeral 77, the beam of rays emergent from the compact LCD 77 by the reference numeral 78, the fixed section of the image projecting optical system by the reference numeral 79, the collimating optical system by the reference numeral 80, the beam of parallel rays by the reference numeral 81, the movable section of the image projecting optical system by the reference numeral 82, the imaging optical system by the reference numeral 83, the center axis of the beam of parallel rays 81 by the reference numeral 84, and the image surface provided for observation via eyepiece by the reference numeral 85.

Figure 11A:
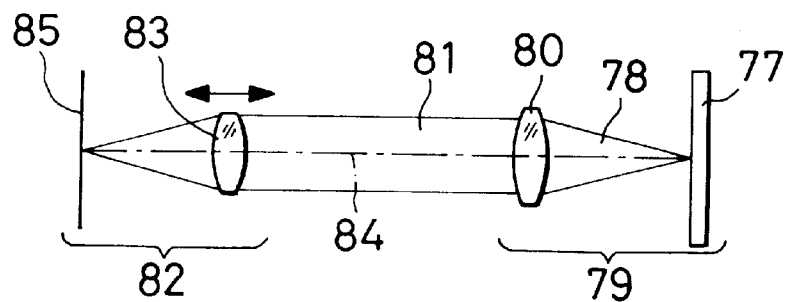
FIG. 11A is a view for explaining the optical principle of the second embodiment shown in FIG. 9, illustrating a condition where the imaging optical system is disposed in the normal position.
Figure 11B:
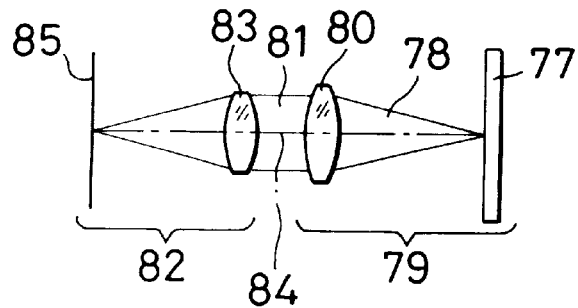
FIG. 11B is a view for explaining the optical principle of the second embodiment, illustrating a condition where the imaging optical system is shifted along the optical axis.

As shown in FIGS. 11A and 11B, since the beam of rays 78 emergent from the compact LCD 77 is transmitted through the collimating optical system 80 to become the beam of parallel rays 81, the imaging optical system 83 in the movable section can receive the beam from the compact LCD 77 in a constant condition even if it slides along its own optical axis, which is aligned to the central axis 84 of the beam of parallel rays 81. Also, since the image surface 85 slides integral with the imaging optical system 83, the imaging optical system 83 constantly forms an image derived from the electronic image at a predetermined position on the image surface 85.

In the image projecting optical systems 69 used in the second embodiment, prisms and mirrors are configured to reflect rays as illustrated in FIG. 8 and 9. According to this configuration, even if the movable sections 82 (FIGS. 11A and 11B) of the image projecting optical system moves in accordance with the adjustment of interpupillary distance of the binocular eyepiece, the electronic images displayed on the compact LCDs 67s are constantly projected in their proper attitudes (without rotation) onto predetermined portions 86 in the image surfaces 68.

The operating microscope according to the second embodiment also is used with an endoscope 37 provided with CCD as shown in FIG. 5. The endoscope 37 with a CCD cooperates with the operating microscope so as to facilitate observation of a narrow cavity interior 36 located in parts 51 under operation, which is not observable by the operating microscope alone. If an electronic image picked up by the endoscope 37 is displayed on the compact LCDS 67 of the image projecting optical systems 69 (FIGS. 8 and 9), the electronic images displayed on the compact LCDs 67 also are projected onto the left and right image surfaces as to follow the same, which are constructed to be movable for adjustment of interpupillary distance of the binocular section 48, and thereby an observer 50 can observe an operating-microscopic image 39 and an endoscopic image 40 simultaneously within an observation field 38 formed by the right and left eyepiece optical systems 64 (FIGS. 8, 9 and 10). Also, if the endoscope 37 is constructed to allow three-dimensional observation, not only the operating-microscopic image 39 but also the endoscopic image 40 can be observed stereoscopically.

In addition, according to the second embodiment, since the compact LCDs 67, the collimating optical systems 70, the mirrors 71 and the prisms 72, which occupy a considerable space in a binocular housing, are fixedly positioned as shown in FIGS. 8 and 9, the housing is not required to provide an extra space for their movement and accordingly, a compact operating microscope with high operability is realized while achieving the above-mentioned advantage, i.e. simultaneous observation of the operating-microscopic image and the endoscopic image.

Figure 12:
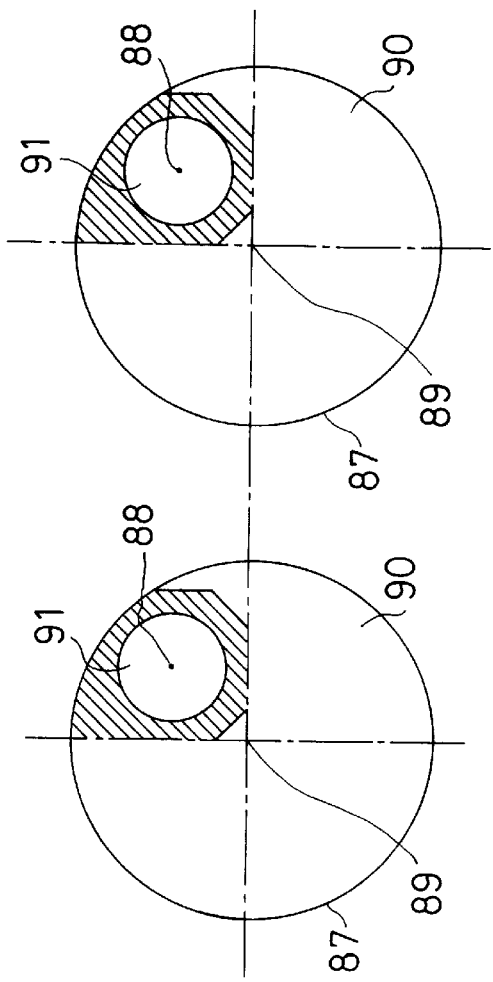
FIG. 12 shows right and left images for observation via binocular eyepiece according to the second embodiment, where images by the image projecting optical system are incorporated.

Next, in reference to FIG. 12, description will be made of the images provided for observation via left and right eyepieces of the operating microscope according to the second embodiment. According to FIG. 12, the observation fields formed by the eyepieces of the operating microscope are represented by the reference numeral 87, the operating-microscopic images by the reference numeral 90, and the endoscopic images by the reference numeral 91.

The image projecting optical systems 69 (FIGS. 8 and 9) of the second embodiment project the electronic images displayed on the compact LCDs 67 (FIGS. 8 and 9) onto the left and right image surfaces 68 (FIGS. 8 and 9) so that the endoscopic images 91 are located at peripheral portions 88 in the upper-right quadrants of the observation fields 87. As a result, the vicinities of field centers 89 of the observation fields 87 of the microscope are reserved for the operating-microscopic images 90.

According to this configuration, observation of the operating-microscopic images 90, which are the principal, is compatible with observation of the endoscopic images 91, which serve as the auxiliary, and in addition, the observer can integrate visual information via the left and right eyes not only with respect to the operating-microscopic image 90 but also to the endoscopic image 91. On the other hand, since an object located in the vicinity of the field center 89 is used as a target to be in focus by an auto-focusing device, it is necessary in using a microscope with auto-focusing function that the vicinity of the field center 89 is occupied by the operating-microscopic image. The image arrangement in the observation field according to the second embodiment is preferable also in that it would not affect auto-focus function.

According to the second embodiment, the electronic images displayed on the compact LCDs 67 (FIGS. 8 and 9) are projected onto the left and right image surfaces of the operating-microscopic optical system. The configuration may be modified so that only one of the image surfaces receives the electronic image.

Also, the electronic images displayed on the compact LCDs 67 (FIGS. 8 and 9) are not necessarily limited to those obtained from the endoscope. Images derived from other image pickup optical system such as a video camera are applicable, or there may be directly displayed electronically produced images such as pictures created by computer graphics or waveform displays obtained from a nerve monitor, which is indispensably used in certain operations.

Also, the compact LCDs (FIGS. 8 and 9) used in the first embodiment may be replaced by other electronic image display means, such as plasma displays.

Furthermore, the image projecting optical systems 69 (FIGS. 8 and 9) and the operating-microscopic optical system of the second embodiment are provided independent of each other, without any common constituent optical element until the image surfaces. Therefore, these optical systems do not degrade images formed by each other, and thus both the images can be viewed clearly.

Figure 13:
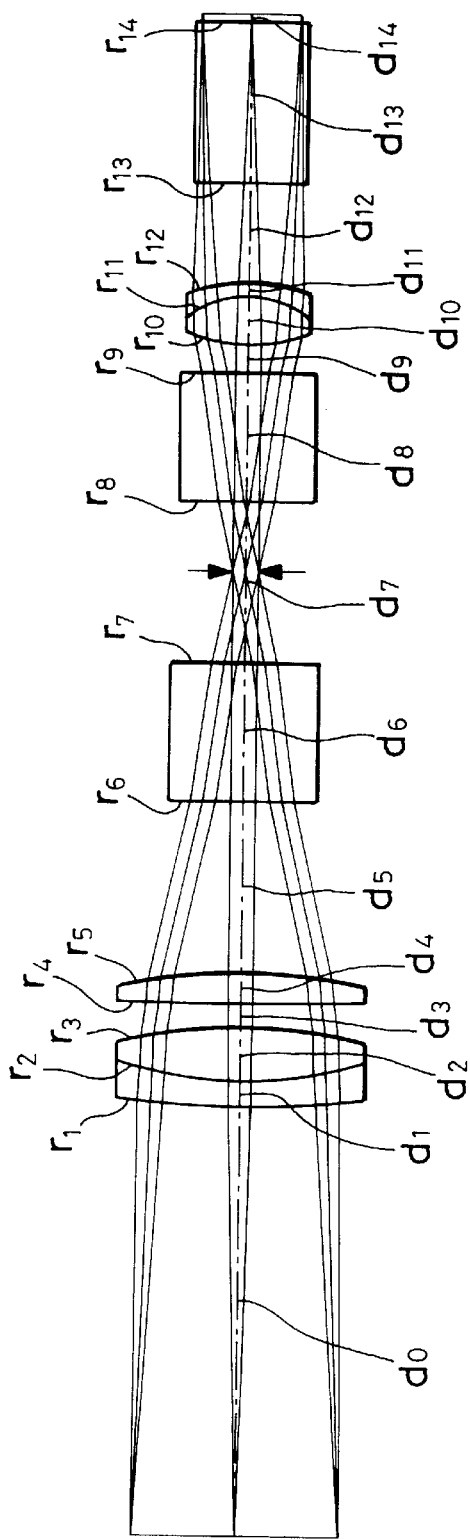
FIG. 13 illustrates in detail an image projecting optical system used in the first and second embodiments.

The following is numerical data of an image projecting optical system applied to the first and second embodiments. Also, FIG. 13 illustrates this image projecting optical system in detail.

| object point | | | |
|---|---|---|---|
| | $d_0 = 36.5711$ | | |
| $r_1 = 85.0398$ | | | |
| | $d_1 = 2.1$ | $n_1 = 1.76182$ | $v_1 = 26.52$ |
| $r_2 = 29.4024$ | | | |
| | $d_2 = 4.5$ | $n_2 = 1.51633$ | $v_2 = 64.14$ |
| $r_3 = -40.1071$ | | | |
| | $d_3 = 2.0$ | | |
| $r_4 = 492.0841$ | | | |
| | $d_4 = 2.5$ | $n_4 = 1.51742$ | $v_4 = 52.43$ |
| $r_5 = -51.2531$ | | | |
| | $d_5 = 15.0$ | | |
| $r_6 = \infty$ | | | |
| | $d_6 = 12.0$ | $n_6 = 1.56883$ | $v_6 = 56.36$ |
| $r_7 = \infty$ | | | |
| | $d_7 = 6\sim21.5536$ | | |
| $r_8 = \infty$ | | | |
| | $d_8 = 11.0$ | $n_8 = 1.56883$ | $v_8 = 56.36$ |
| $r_9 = \infty$ | | | |
| | $d_9 = 2.4$ | | |
| $r_{10} = 14.2721$ | | | |
| | $d_{10} = 4.0$ | $n_{10} = 1.51742$ | $v_{10} = 52.43$ |
| $r_{11} = -8.0096$ | | | |
| | $d_{11} = 1.1$ | $n_{11} = 1.76182$ | $v_{11} = 26.52$ |
| $r_{12} = -16.5120$ | | | |
| | $d_{12} = 8.5$ | | |
| $r_{13} = \infty$ | | | |
| | $d_{13} = 14.0$ | $n_{13} = 1.56883$ | $v_{13} = 56.36$ |
| $r_{14} = \infty$ | | | |
| | $d_{14} = 0.5$ | | |
| image point | | | |

Figure 14:
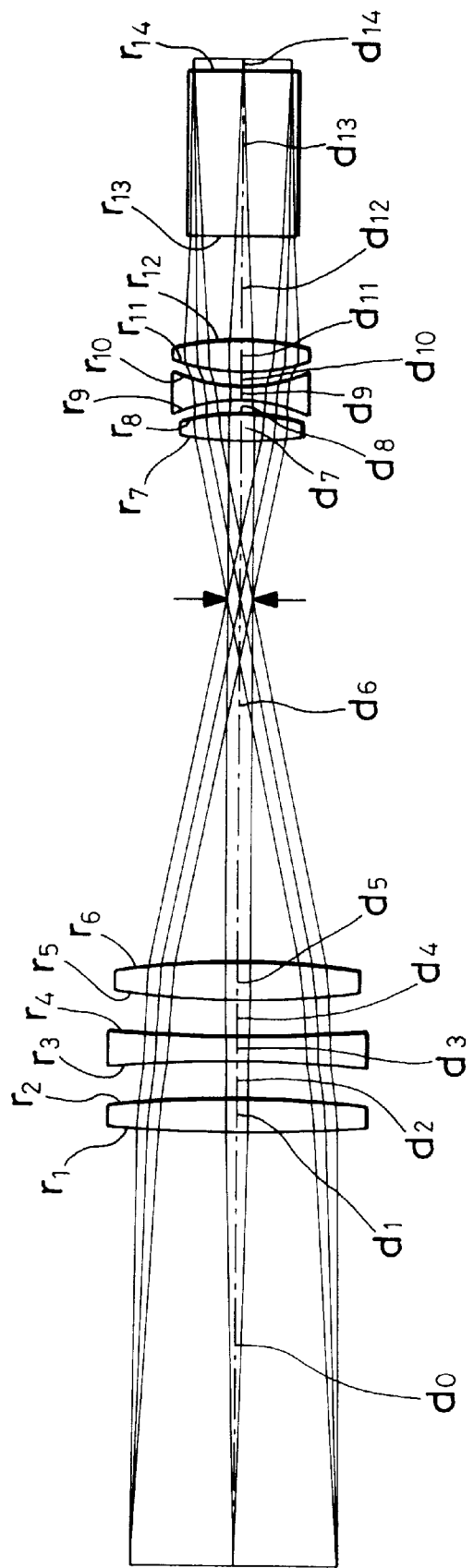
FIG. 14 illustrates in detail another image projecting optical system (compatible with high-image-quality LCD) alternatively used in the first and second embodiments.

Also, the following is numerical data of an image projecting optical system (compatible with high-image-quality LCD) applied to the first and second embodiments. Also, FIG. 14 illustrates this image projecting optical system in detail.

| object point | | | |
|---|---|---|---|
| | $d_0 = 36.5$ | | |
| $r_1 = 112.1074$ | | | |
| | $d_1 = 2.8$ | $n_1 = 1.81600$ | $v_1 = 46.62$ |
| $r_2 = -112.1074$ | | | |
| | $d_2 = 3.1$ | | |
| $r_3 = -129.102$ | | | |
| | $d_3 = 2.2$ | $n_3 = 1.84666$ | $v_3 = 23.78$ |
| $r_4 = 129.102$ | | | |
| | $d_4 = 3.1$ | | |
| $r_5 = 72.0703$ | | | |
| | $d_5 = 3.2$ | $n_5 = 1.81600$ | $v_5 = 46.62$ |
| $r_6 = -72.0703$ | | | |
| | $d_6 = 36.5\sim52.05635$ | | |
| $r_7 = 39.0847$ | | | |
| | $d_7 = 2.2$ | $n_7 = 1.88300$ | $v_7 = 40.76$ |

-continued

| | | | |
|---|---|---|---|
| $r_8 = -19.1041$ | | | |
| | $d_8 = 1.2$ | | |
| $r_9 = -12.4648$ | | | |
| | $d_9 = 1.2$ | $n_9 = 1.72151$ | $v_9 = 29.23$ |
| $r_{10} = 12.4648$ | | | |
| | $d_{10} = 1.2$ | | |
| $r_{11} = 15.7439$ | | | |
| | $d_{11} = 2.7$ | $n_{11} = 1.88300$ | $v_{11} = 40.76$ |
| $r_{12} = -25.2987$ | | | |
| | $d_{12} = 8.97$ | | |
| $r_{13} = \infty$ | | | |
| | $d_{13} = 14.0$ | $n_{13} = 1.56883$ | $v_{13} = 56.36$ |
| $r_{14} = \infty$ | | | |
| | $d_{14} = 0.7667$ | | |
| image point | | | |

Third Embodiment

In reference to FIG. 15, description will be made of the third embodiment, according to which a light intercepting member is disposed in the moving section of such an image projecting optical system as used in the first or second embodiment. In FIG. 15, the reference numeral 92 represents a light intercepting member, the reference numeral 93 represents an image surface provided for observation via eyepiece, the reference numeral 94 represents an eyepiece optical system, the reference numeral 95 represents a pupil of the observer, and the symbol O represents an imaging point.

According to the third embodiment, a light intercepting member 92 is arranged in the movable section 26 (FIG. 3), 82 (FIGS. 11A and 11B), which is moved in accordance with adjustment of interpupillary distance of the binocular section 48 (FIG. 5), of the image projecting optical system 9 (FIG. 1), 69 (FIGS. 8 and 9) of the first and second embodiment, to intercept a part of the light beam used to form the operating-microscopic image 90 (FIG. 12), i.e. to cause a partial eclipse in the operating-microscopic image 90. The third embodiment arranges the image projecting optical system 9, 69 in such a manner that the electronic image displayed on the compact LCD 34 (FIG. 4), 67 (FIG. 8) is projected at a position in this eclipsed portion of the operating-microscopic image 90. As shown in FIG. 15, the light intercepting member 92 serves as a reflecting member also for reflecting the beam emergent from the compact LCD, to save a space inside the binocular housing 5 (FIG. 1). According to the above-described configuration, since the operating-microscopic image 55 (FIG. 6) and the endoscopic image 56 (FIG. 6) do not overlap with each other, the observer can observe both the images simultaneously and clearly.

If the compact LCD 34 is provided with an image other than the endoscopic image, for example, a waveform display of the nerve monitor or the like, the light intercepting member 92 may be replaced by a half mirror, because such an image can be satisfactorily observed even if overlapping with the operating-microscopic image.

Fourth Embodiment

In reference to FIG. 16, description will be made of the fourth embodiment, according to which a movable prism is disposed in the movable section of such an image projecting optical system as used in the first or second embodiment. In FIG. 16, the reference numeral 97 represents a movable prism, and the reference numeral 98 represents the movable prism after movement.

According to the fourth embodiment, a movable prism 97 that is constructed to be movable at observer's will is arranged in the movable section 26 (FIG. 3), 82 (FIGS. 11A and 11B), which is moved in accordance with the adjustment of interpupillary distance of the binocular section 48 (FIG. 5), of the image projecting optical system 9 (FIG. 1), 69 (FIGS. 11A and 11B) of the first and second embodiment, so that the observer has an option to shift the endoscopic image 91 (see FIG. 12) out of the observation field by displacing the movable prism 97. According to this configuration, if the observer judges the endoscopic image unnecessary, it can be removed from the observation field.

Fifth Embodiment

Figure 17:
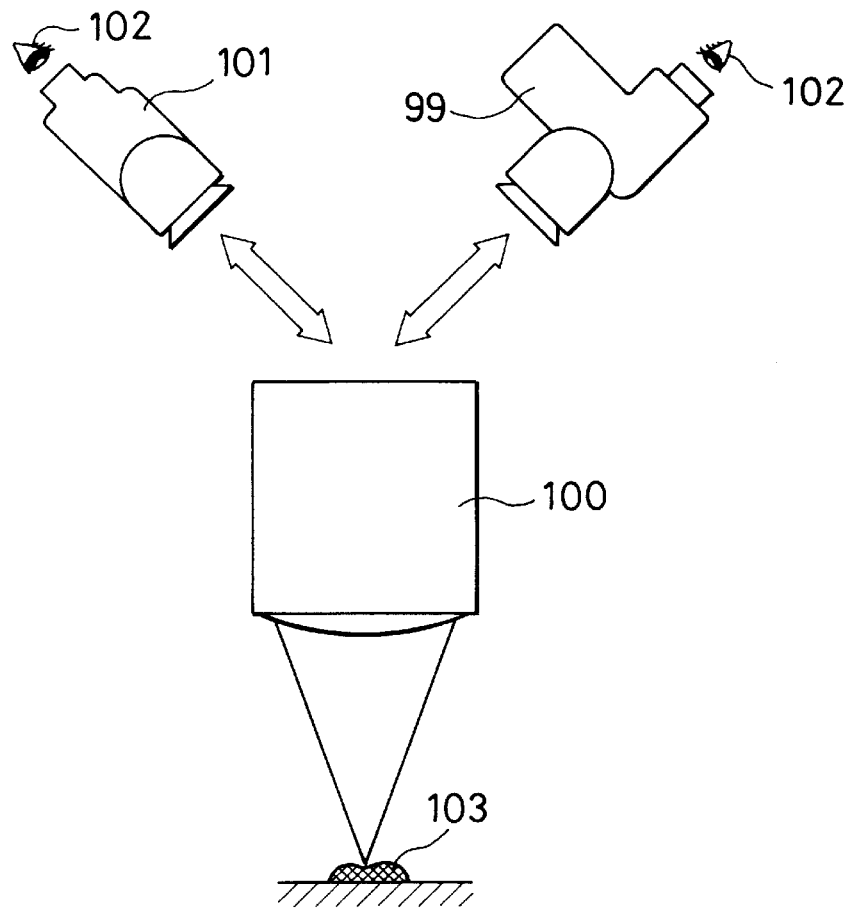
FIG. 17 is directed to the fifth embodiment of the present invention, showing that a binocular optical system inclusive of left and right eyepiece optical systems, an image projecting optical system, and a compact LCD are housed in a binocular housing similar to that used in the first or second embodiment to form an integral binocular unit, which is constructed to be removably mounted on the main housing of the operating microscope.

According to the fifth embodiment, as shown in FIG. 17, a binocular unit 99 incorporating therein a binocular optical system 6 inclusive of a pair of left and right eyepiece optical systems 18, an image projecting optical system, and a compact LCD 7, which are all shown in FIG. 1, is constructed to achieve removable mount on a main unit 100 of the operating microscope.

According to this configuration, the binocular unit 99 is modularly replaceable with a normal type binocular unit 101 of the operating microscope. Consequently, an observer who does not need simultaneous observation of the operating-microscopic image 39 (FIG. 5) and the endoscopic image 38 (FIG. 5) can observe the operating-microscopic image alone using the normal type binocular unit 101. In a medical facility, one operating microscope is often used in common among, for instance, cerebral neurosurgery, ophthalmology and orthopedics but in different application modes. Modular replacement of the binocular units realizes an operating microscope that meets various requirements which differ by clinical specialty.

Sixth Embodiment

Figure 18:
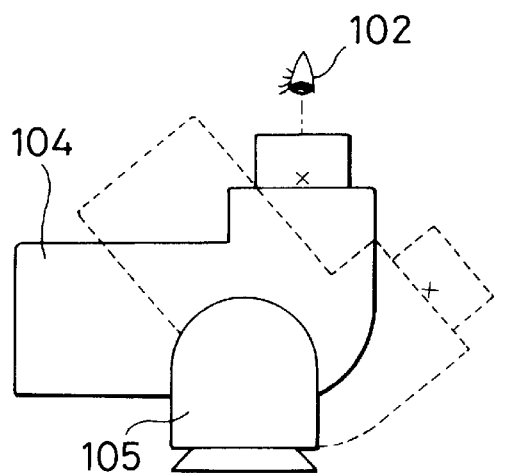
FIG. 18 is directed to the sixth embodiment of the present invention, showing that a binocular section of the operating microscope similar to that used in the first or second embodiment is constructed to have variable inclination angle, and that the image projecting optical system is built in a movable housing.

FIG. 18 is directed to the sixth embodiment of the present invention. According to the sixth embodiment, a movable housing 104 and a fixed housing 105 constitute a binocular section of the operating microscope, which is an analogue of the binocular section 48 shown in FIG. 5, so that the binocular section has variable inclination angle. Furthermore, the image projecting optical system 9 (FIG. 1) is housed in the movable housing 104. According to this configuration, when the image surfaces provided for observation via eyepiece shift in accordance with change of inclination angle, the image projecting optical 9 moves integral with the image surfaces, without changing its position relative to the image surfaces. Hence, it is not necessary to provide an additional mechanism to make the image projecting optical system 9 follow the movement of the image surfaces. The sixth embodiment thus can prevent extra bulkiness of the operating microscope.

Seventh Embodiment

Figure 19:
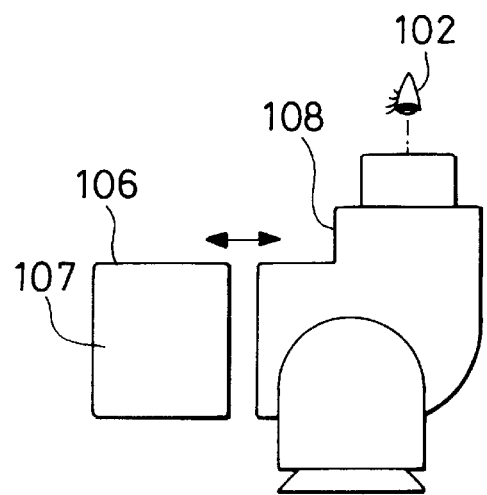
FIG. 19 is directed to the seventh embodiment of the present invention.

FIG. 19 is directed to the seventh embodiment of the present invention. According to the seventh embodiment, the compact LCD 7 (FIG. 1) and the image projecting optical system 9 (FIG. 1) are housed in a housing 106 to form an image projecting unit 107. Furthermore, the image projecting unit 107 is constructed to be removably mounted on a binocular housing 108 that houses an ordinary binocular optical system.

The seventh embodiment achieves the same effect as obtained by the fifth embodiment only with engagement and disengagement of the image projecting optical unit 107; replacement of the binocular housing 108 is not needed.

Eighth Embodiment

FIGS. 20A, 20B, 21A, 21B are directed to the eighth embodiment of the present invention.

According to the eighth embodiment, a pair of left and right trapezoidal prisms P are so arranged in a binocular optical system 6 (FIG. 1) of the operating microscope used in the first or second embodiment as to reflect rays three-times inside themselves. In the operating microscope according to the present invention, it is necessary to secure a space to accommodate the image projecting optical system 9 (FIG. 1) inside or adjacent to the binocular housing 5 (FIG. 1). Therefore, optical components constituting the binocular optical system 6 (FIG. 1) are required to be small as much as possible. This requirementismoreurgentwith respecttoprisms, which occupy relatively large space, specifically with respect to a trapezoidal prism Q (FIG. 22A), which is arranged to reflect rays twice inside itself to turn the travelling direction of the rays by 180°. According to the eighth embodiment, the trapezoidal prism Q for two-times reflection is replaced by a trapezoidal prism P (FIG. 22B) so as to reduce the size of the binocular optical system 6 in the direction of prism thickness. Consequently, a compact and highly operable binocular section provided with image projecting function is realized.

Also, if an ordinary binocular section of an operating microscope employs the above-mentioned prism configuration of the eighth embodiment, it also can reduce its size.

The following is numerical data of the binocular optical section shown in FIGS. 20A and 20B provided with Siedentoph system for adjustment of interpupillary distance.

| | | | |
|---|---|---|---|
| $r_1 = 36.53$ | | | |
| | $d_1 = 1.9$ | $n_1 = 1.60342$ | $v_1 = 38.03$ |
| $r_2 = \infty$ | | | |
| | $d_2 = 5.1$ | | |
| $r_3 = 75.245$ | | | |
| | $d_3 = 2.4$ | $n_3 = 1.51633$ | $v_3 = 64.14$ |
| $r_4 = -30.385$ | | | |
| | $d_4 = 1.6$ | $n_4 = 1.58144$ | $v_4 = 40.75$ |
| $r_5 = 30.385$ | | | |
| | $d_5 = 22.5$ | | |
| $r_6 = \infty$ | | | |
| | $d_6 = 25.607$ | $n_6 = 1.56883$ | $v_6 = 56.36$ |
| $r_7 = \infty$ | | | |
| | $d_7 = 1.132$ | | |
| $r_8 = \infty$ | | | |
| | $d_8 = 45.244$ | $n_8 = 1.56883$ | $v_8 = 56.36$ |
| $r_9 = \infty$ | | | |
| | $d_9 = 8.0$ | | |
| $r_{10} = \infty$ | | | |
| | $d_{10} = 55.426$ | $n_{10} = 1.51633$ | $v_{10} = 64.14$ |
| $r_{11} = \infty$ | | | |
| | $d_{11} = 1.0$ | | |
| $r_{12} = \infty$ | | | |
| | $d_{12} = 22.0$ | $n_{12} = 1.56883$ | $v_{12} = 56.36$ |
| $r_{13} = \infty$ | | | |
| | $d_{13} = 7.931$ | | |
| $r_{14} = \infty$ | | | |
| | $d_{14} = 58.5$ | $n_{14} = 1.56883$ | $v_{14} = 56.36$ |
| $r_{15} = \infty$ | | | |
| 0 (image point) | | | |

Also, the following is numerical data of the binocular optical section shown in FIGS. 21A and 21B provided with Jentzsche system for adjustment of interpupillary distance.

| | | | |
|---|---|---|---|
| $r_1 = 35.1815$ | | | |
| | $d_1 = 2.4$ | $n_1 = 1.51742$ | $v_1 = 52.43$ |
| $r_2 = -24.3244$ | | | |
| | $d_2 = 1.6$ | $n_2 = 1.62588$ | $v_1 = 35.70$ |
| $r_3 = -76.5057$ | | | |
| | $d_3 = 9.5$ | | |
| $r_4 = 1840.6599$ | | | |
| | $d_4 = 1.6$ | $n_4 = 1.51633$ | $v_4 = 64.14$ |
| $r_5 = 29.1137$ | | | |
| | $d_5 = 11.5$ | | |

-continued

| | | | |
|---|---|---|---|
| $r_6 = \infty$ | | | |
| | $d_6 = 25.607$ | $n_6 = 1.56883$ | $v_6 = 56.36$ |
| $r_7 = \infty$ | | | |
| | $d_7 = 1.132$ | | |
| $r_8 = \infty$ | | | |
| | $d_8 = 45.239$ | $n_8 = 1.56883$ | $v_8 = 56.36$ |
| $r_9 = \infty$ | | | |
| | $d_9 = 8.0$ | | |
| $r_{10} = \infty$ | | | |
| | $d_{10} = 71.014$ | $n_{10} = 1.56883$ | $v_{10} = 56.36$ |
| $r_{11} = \infty$ | | | |
| | $d_{11} = 10.0$ | | |
| $r_{12} = \infty$ | | | |
| | $d_{12} = 24.0$ | $n_{12} = 1.56883$ | $v_{12} = 56.36$ |
| $r_{13} = \infty$ | | | |
| | $d_{13} = 15.1032$ | | |
| 0(image point) | | | |

In the numerical data of the embodiments mentioned above, $r_1, r_2, \ldots$ represent radii of curvature of individual lens or prism surfaces; $d^1, d_2, \ldots$ thicknesses of individual lenses or prisms, or spaces therebetween; $n^1, n_{21} \ldots$ refractive indices of individual lenses or prisms; $v^1, v_2, \ldots$ Abbe's numbers of individual lenses or prisms.

Ninth Embodiment

FIG. 23 is directed to the ninth embodiment of the present invention. In FIG. 23, is the reference numeral 110 represents an eyepiece optical system, the reference numeral 110 represents an exit pupil of the operating-microscopic optical system, the reference numeral 111 represents an exit pupil of the image projecting optical system, the reference numeral 112 represents an eyepoint of the operating microscope, the reference numeral 113 represents an operating-microscopic image, and the reference numeral 114 represents an electronic image as projected from the compact LCD 7.

According to the ninth embodiment, the operating microscope similar to that of the first or second embodiment is arranged so that the exit pupil 111 of the image projecting optical system 9 (FIG. 1) is formed via the eyepiece optical system 109 at the same position as the exit pupil 110 of the operating-microscopic optical system but to have the diameter of 3 mm, which is larger than that of the exit pupil 110 of the operating-microscopic optical system.

According to this pupil arrangement, when an observer sets the eye at the eyepoint 112 of the operating microscope, the electronic image 114 as projected onto the image surface of the operating-microscopic optical system and the operating-microscopic image 113 are simultaneously observable.

In general, the operating-microscopic image 113 has a higher luminance than that of the electronic image 114 on the image surface, and thus the observer often feels that the electronic image is darker than the operating-microscopic image. According to the ninth embodiment, however, apparent difference in brightness is not so distinctive, because diameter of the exit pupil 111 of the image projecting optical system 9 is set to, 3 mm so as to be larger than not only that of the exit pupil 110 of the operating microscopic optical system but also the human pupil diameter of 2.5 mm.

Tenth Embodiment

Figure 24A:
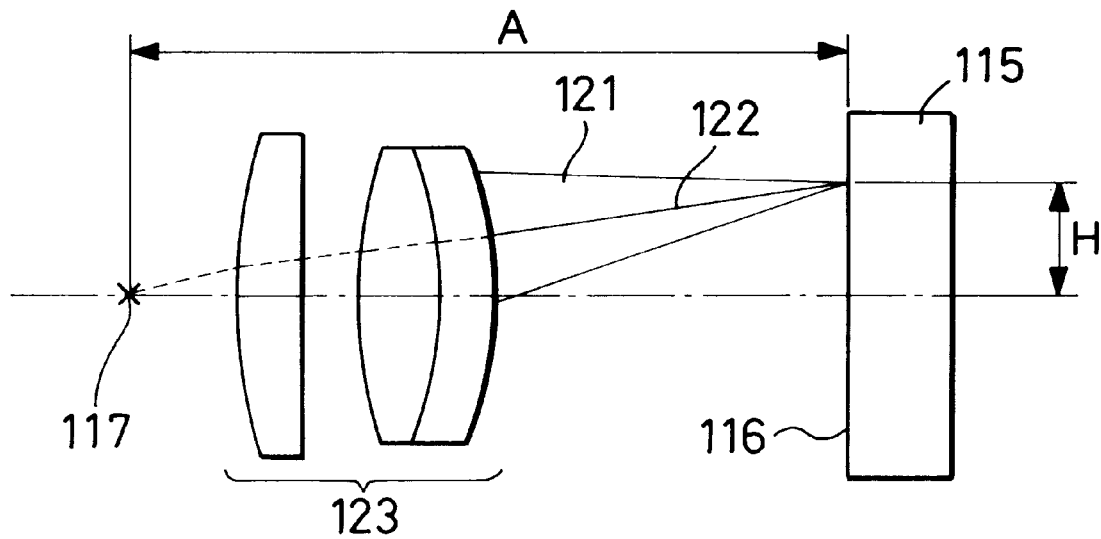
FIG. 24A shows optical arrangement according to the tenth embodiment of the present invention.
Figure 24B:
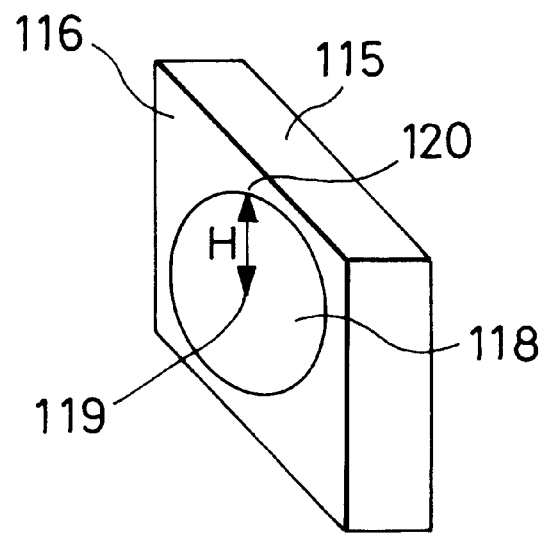
FIG. 24B is a perspective view of the compact LCD used in the tenth embodiment.

In reference to FIGS. 24A and 24B, description will be made of the tenth embodiment of the present invention. In FIGS. 24A and 24B, the reference numeral 115 represents a compact LCD, the reference numeral 116 represents a display surface of the compact LCD 115, the reference numeral 117 represents an entrance pupil of the image projecting optical system 9 (FIG. 1), the reference numeral 118 represents an endoscopic image displayed on the display surface 116, the reference numeral 119 represents the center point of the endoscopic image 118, the reference numeral 120 represents the periphery of the endoscopic image 118, the reference numeral 121 represents a beam of rays emergent from the display surface 116 of the compact LCD 115 and incident on the image projecting optical system 9, the reference numeral 122 represents a principal ray of the beam 121, and the reference numeral 123 represents a collimating optical system of the image projecting optical system 9.

According to the tenth embodiment, the image projecting optical system 9 similar to that of the first or second embodiment is a constructed so that the endoscopic image 118 displayed on the display surface 116 of the compact LCD 115 has a circular contour with diameter of 16.8 mm, and the position of the entrance pupil 117 of the image projecting optical system 9 is determined to be distant from the display surface 116 of the compact LCD 115 at least by 68.5 mm.

This arrangement is based on the condition:

$$A \geq (H/\tan 7°)$$

where A is a distance from the display surface 116 of the compact LCD 115 to the entrance pupil of the image projecting optical system 9, and H is a distance from the center point 119 to the periphery 120 of the endoscopic image 118 on the display surface 116. In the case of the tenth embodiment, A=100 and H=8.4, and thus the above numerical condition is satisfied.

When this numerical condition is satisfied, the principal ray 122 of the beam 121 to be incident on the image projecting optical system is not so oblique with respect to the display surface 116 of the compact LCD 115. Therefore, even if the compact LCD 115 does not have excellent angular range characteristic in color tone reproducibility, the entire image can be observed in good color tone condition.

Eleventh Embodiment

Figure 25A:
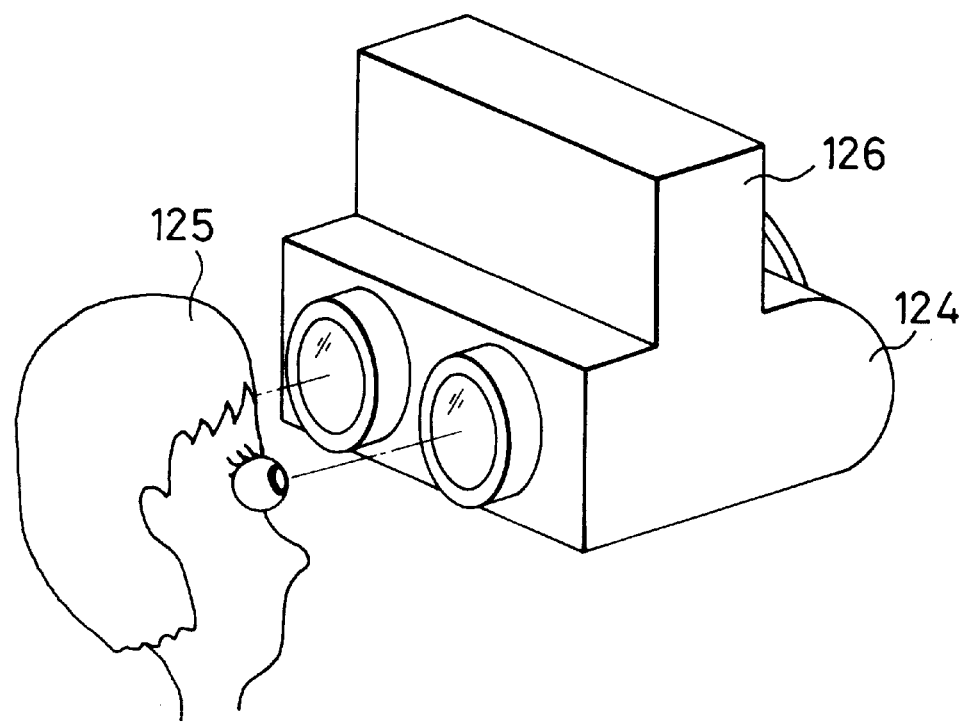
FIG. 25A is an overview of a binocular unit according to the eleventh embodiment of the present invention.
Figure 25B:
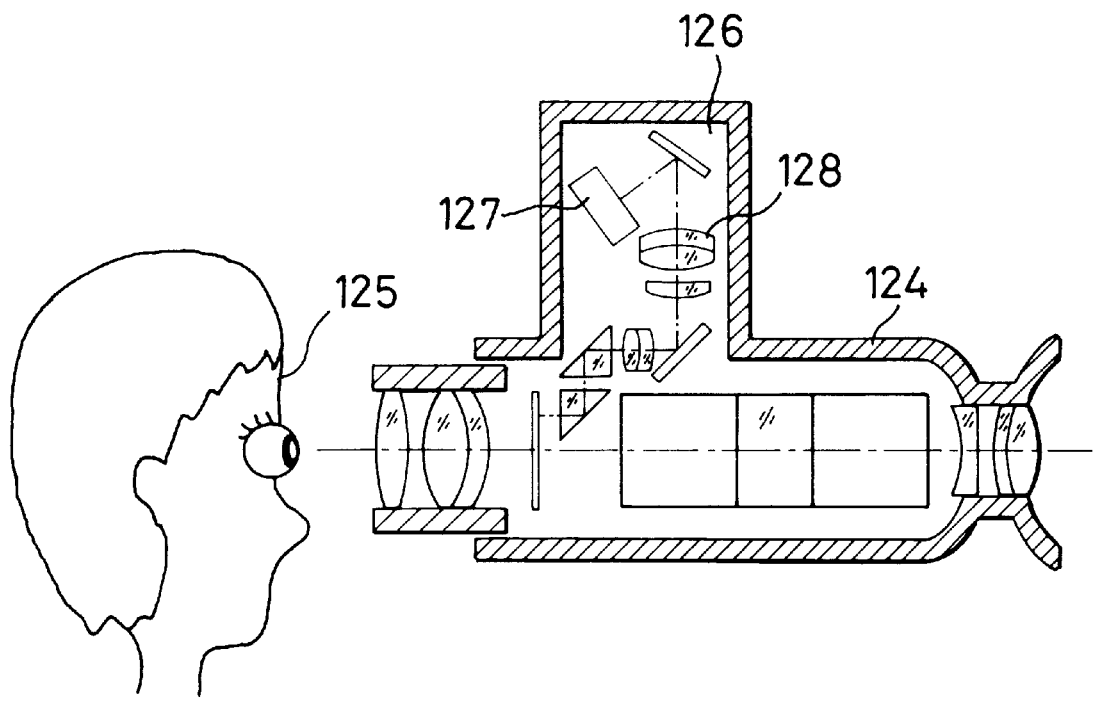
FIG. 25B is a cross-sectional view of the binocular unit shown in FIG. 25A.

In reference to FIGS. 25A and 25B, description will be made of the eleventh embodiment of the present invention. As shown in FIGS. 25A and 25B, according to the eleventh embodiment, a binocular housing 124 is provided with a space for accommodating a pair of compact LCDs 127 and a pair of image projecting optical systems 128 at a position to face the forehead 125 of an observer who looks into the binocular eyepiece.

According to this arrangement, the binocular housing 124 presents its bulkiness necessitated by the built-in LCD 127s and the image projecting optical systems 128 only in the upward direction, free from any other projecting portions in the downward direction to approach the observer's hands or in the lateral directions. Consequently, the binocular housing 124 would not be the obstruct to the operation and thus loss of work efficiency is obviated.

The above-described first to eleventh embodiments are also applicable to those stereomicroscopes used for purposes other than surgical operation, to attain the same effects as described above.

Twelfth Embodiment

Figure 26:
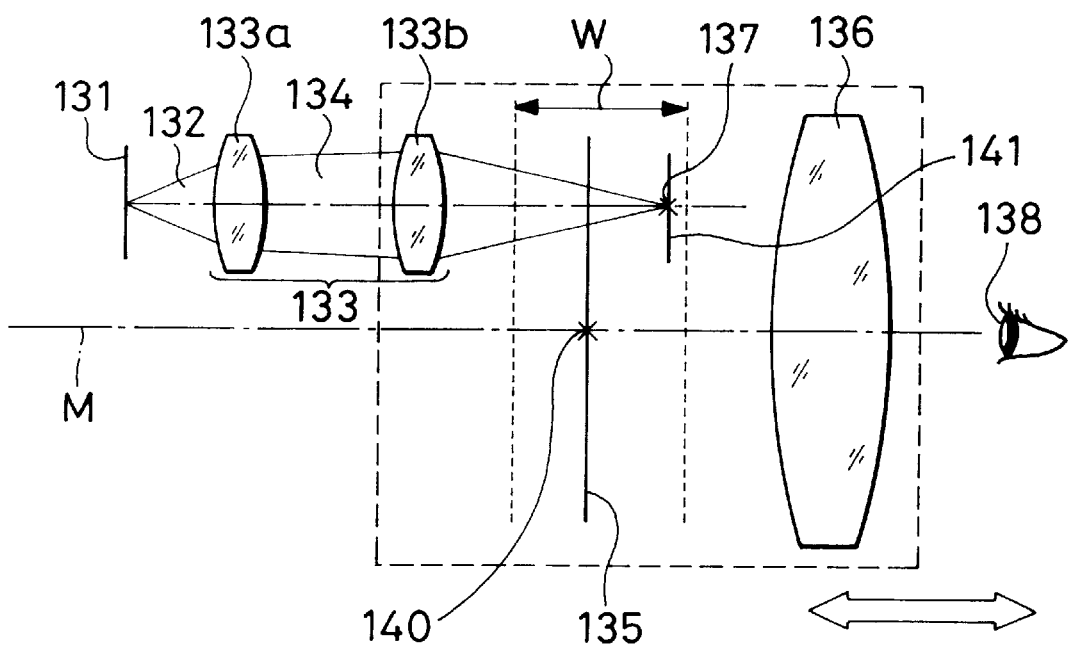
FIG. 26 shows optical arrangement according to the twelfth embodiment of the present invention.

FIG. 26 is directed to the eleventh twelfth embodiment of the present invention. The operating microscope according to the twelfth embodiment comprises an image projecting optical system for introducing an image derived from an endoscopic optical system, which is provided separate from an operating-microscopic optical system, into an eyepiece optical system of the operating microscope so that the operating-microscopic image and the endoscopic image can be simultaneously observed. As shown in FIG. 26, a beam of rays 132 emergent from the endoscopic image 131 is converted into a beam of divergent rays 134 via a first lens unit 133a of an image projecting optical system 133. A second lens unit 133b of the image projecting optical system 133 receives the beam of divergent rays 134 to form an image while moving in a direction of an optical axis M integral with an eyepiece optical system 136 in accordance with adjustment of interpupillary distance. An imaging position 137 by the image projecting optical system 133 is shifted from an image surface 135, which is predetermined for observation via eyepiece, in accordance with the adjustment of interpupillary distance. However, since the shift of the imaging position occurs within a range W of focal depth of an observer's eye 138, the observer can observe the operating-microscopic image 140 and the endoscopic image 141 on the image surface 135 simultaneously and clearly also. In the twelfth embodiment, the beam of rays emergent from the first lens unit 133a of the image projecting optical system 133 is designed to be divergent. However, the arrangement may be modified so that the beam of rays is convergent.

In the operating microscope according to the twelfth embodiment, a part of the image projecting optical system 133 is movable within a range as allows an entrance aperture thereof to receive a beam of rays, and a defocus amount of the projected image in reference to the image surface 135 provided for observation via eyepiece, which amount varies with the movement of the part of the image projecting optical system 133, satisfies the following condition:

$$-2((foc^2)/1000) < X < 2((foc^2)/1000)$$

where foc is a focal length of the eyepiece optical system, and X is the defocus amount.

The above condition is set considering focal depth of the observers eyes. If the condition is exceeded, the endoscopic image appears to be out of focus, whereas the operating-microscopic image can be observed in good focus; simultaneous observation of both the images in good focus condition cannot be realized. In contrast, according to the twelfth embodiment, even if the projected image is defocused in reference to the image surface provided for observation via eyepiece in accordance with movement of the part of the image projecting optical system, the defocus amount falls within a range of focal depth of the observer' eyes. Therefore, the operating-microscopic image and the endoscopic image are compatible for observation in the operating microscope.

Thirteenth Embodiment

Figure 27A:
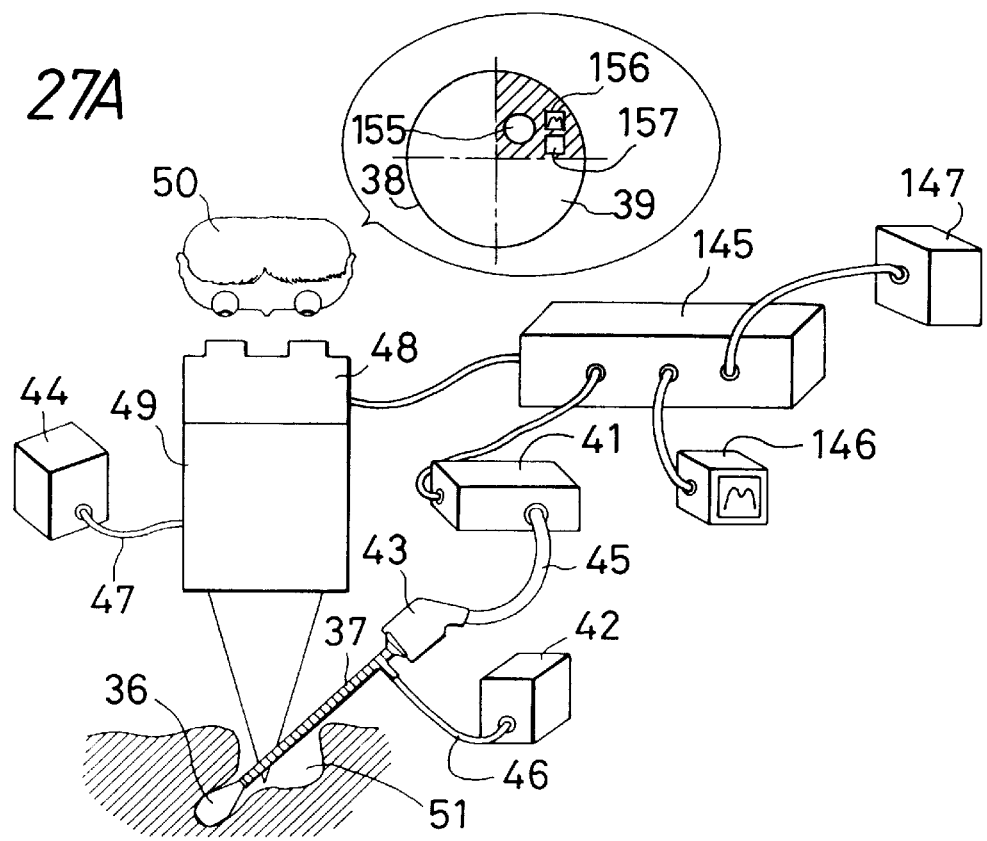
FIG. 27A is a schematic view showing the overall configuration of the thirteenth embodiment of the present invention.
Figure 27B:
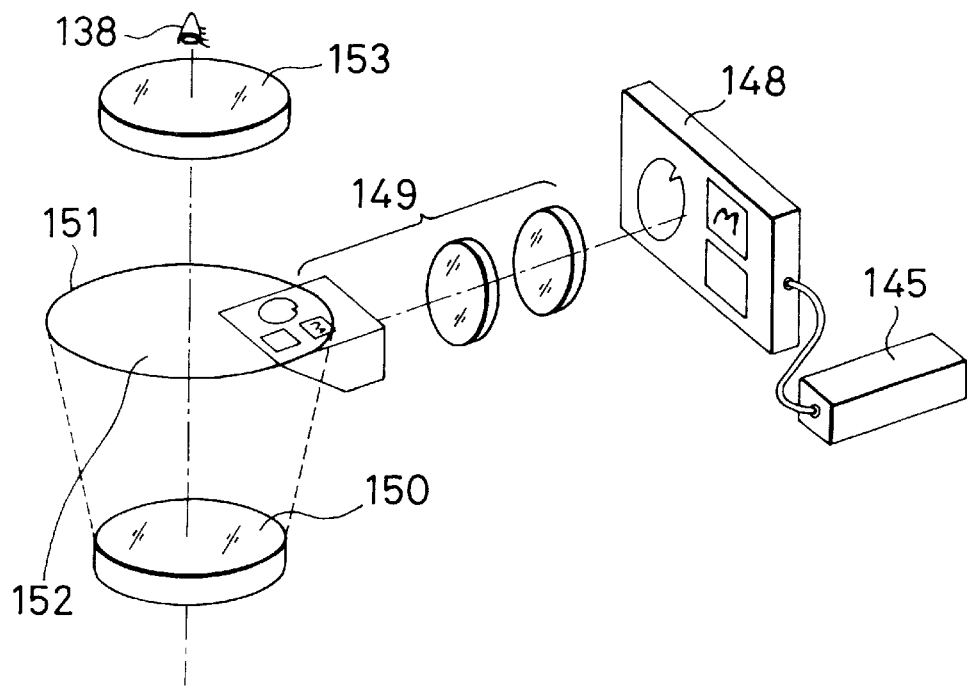
FIG. 27B shows optical systems in the binocular section according to the thirteenth embodiment.

In reference to FIGS. 27A and 27B, description will be made of the thirteenth embodiment of the present invention. According to the thirteenth embodiment, as schematically shown in FIG. 27A, not only an image from an endoscope 37 but also images from a waveform monitor 146, CT 147 etc. are fed to an image processor unit 145 so as to be simultaneously displayed on a single display surface of a compact LCD 148 shown in FIG. 27B. The reference numerals shown in FIG. 27A but not specifically referred to here represent the same devices or elements as represented by the same reference numerals shown in FIG. 5. As shown in FIG. 27B, these plurality of images displayed on the compact LCD 148 are projected by an image projecting optical system 149 onto an image surface 151 included in an operating-microscopic optical system 150 for observation via eyepiece. Consequently, an observer 50 can obtain useful visual information to facilitate the operation such as an endoscopic image 155, a waveform display 156, a CT image 157 etc. along with an operating-microscopic image 152 by observing the images within one observation field 38 as enlarged by an eyepiece optical system 153.

Furthermore, since a plurality of images are displayed on one display surface, to dispense with additional compact LCDs or image projecting optical systems, bulkiness of the housing is avoided and accordingly a compact and highly operable operating microscope can be realized. In the case, although individual images on the display surface are rendered to be small, the observer is able to observe them without difficulty by selecting magnification of the image projecting optical system appropriately. For the compact LCD 148 to display a plurality of images, that having much oblong display surface with aspect ratio of 16:9 is preferable.

Fourteenth Embodiment

Figure 28:
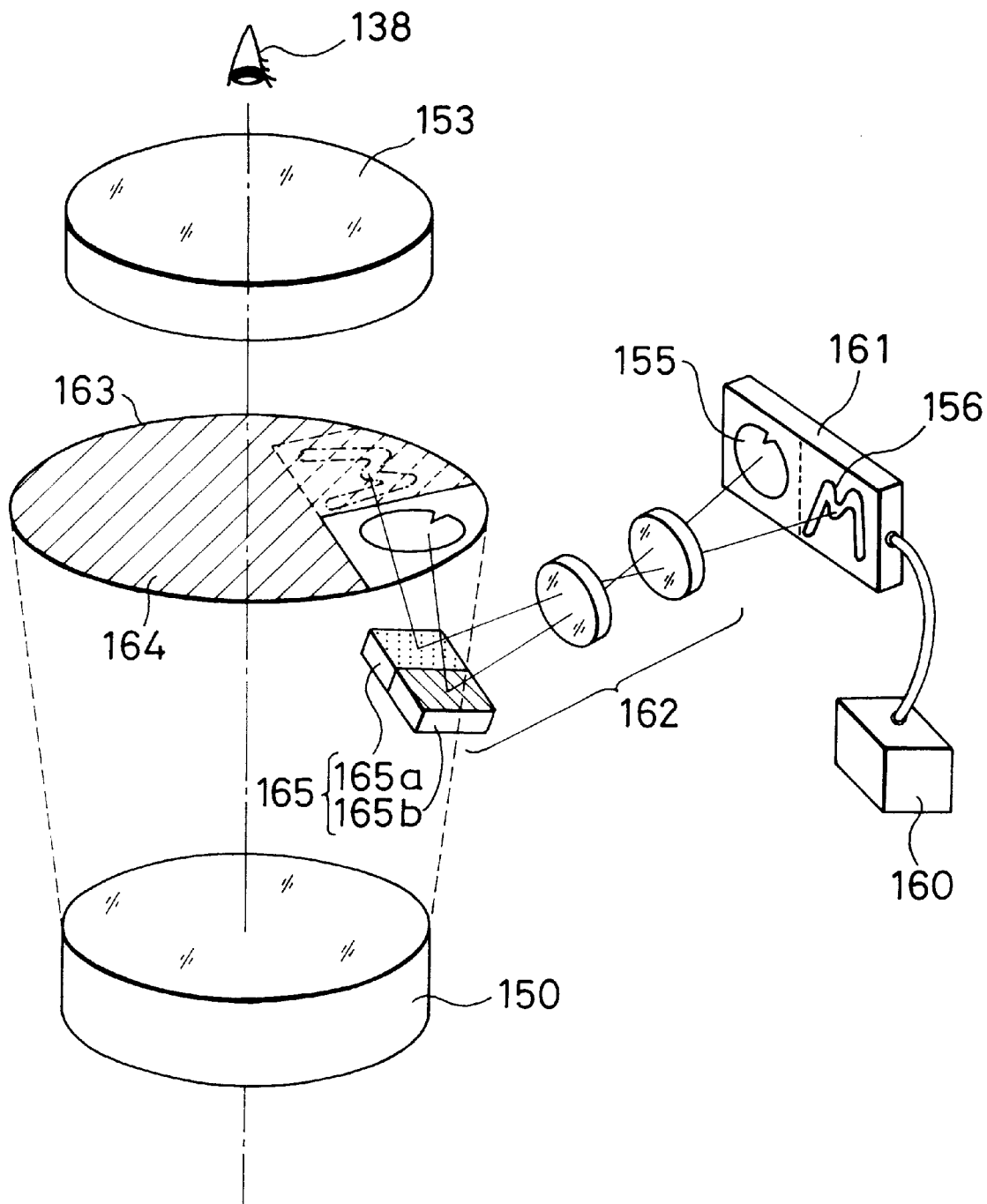
FIG. 28 shows optical systems in a binocular section according to the fourteenth embodiment of the present invention.

FIG. 28 is directed to the fourteenth embodiment of the present invention. An image processor unit 160 according to the fourteenth embodiment is connected with an endoscope 37 (via a camera control unit 41 and a CCD camera adapter for endoscopes 43) and a waveform monitor 146 in the same manner as shown in FIG. 27A, and controls a compact LCD 161 so that an endoscopic image 155 and a waveform display 156 are simultaneously displayed side by side on the display surface of the compact LCD 161. These plurality of images displayed on the compact LCD 161 are projected by an image projecting optical system 162 onto an image surface 163 included in an operating-microscopic optical system 150 for observation via eyepiece. Furthermore, of optical members included in the image projecting optical system, a most image-surface-side reflecting mirror 165 is divided into a half mirror 165a and a full mirror 165b arranged side by side. The former is designed to reflect a beam of rays emergent from the waveform display 156 and the latter is designed to reflect a beam of rays emergent from the endoscopic image 155.

According to the above-described configuration of the fourteenth embodiment, an observer can obtain useful visual information to facilitate the operation such as the endoscopic image 155, the waveform display 156 etc. along with an operating-microscopic image 164 by observing the images within one observation field as enlarged by an eyepiece optical system 153. Furthermore, since a plurality of images are displayed on one display surface, to dispense additional compact LCDs or image projecting optical systems, bulkiness of the housing is avoided and accordingly a compact and highly operable operating microscope can be realized. For the compact LCD 161 to display a plurality of images, that having much oblong display surface with aspect ratio of 16:9is preferable.

Also, according to the configuration of the fourteenth embodiment, since the endoscopic image 155 is projected onto the image surface 163 after being reflected by a mirror or a full reflection prism that is inserted in a beam of rays travelling through the operating-microscopic optical system 150, a portion of the operating-microscopic image 164 located corresponding to the endoscopic image 155 is intercepted by the mirror or the prism and thus is not visible to the observer. Consequently, the operating-microscopic image 164 does not overlap with the endoscopic image 155 on the image surface 163. This arrangement is made considering that both the operating-microscopic image 164 and the endoscopic image 155 carry fine and complicated visual information and thus are likely to spoil each other in overlapping. According to the fourteenth embodiment, the operating-microscopic image 164 and the endoscopic image 155 are distinctively observed under the non-overlap condition. In addition, both the images are free from loss of brightness caused by overlapping, and thus individual bright images can be observed.

On the other hand, the waveform display 156 or a text is rather simple as visual information. Therefore, even if such an image is made to overlap with the operating microscopic image 164, individual images are easily recognizable. Considering this fact, according to the fourteenth embodiment, the waveform display 156 is made to overlap with the operating-microscopic image 164 on the image surface 163 using the half mirror 165. In this arrangement, the waveform display 156 or the text leaves a large area in the observation field to be used for the operating-microscopic image 164 because no portion of the operating-microscopic image 164 is shaded for the purpose of observation of the waveform display 156 or the like, and thus does not impede observation of the operating-microscopic image 164, which is given a higher priority in the operation. Furthermore, by adjusting intensity using the image processor unit 160, the overlapping image such as the waveform display 156 or the text can be highlighted or, for observing the operating-microscopic image 164 alone, erased as required.

What is claimed is:

1. An operating microscope, comprising:

an image projecting optical system for introducing an image derived from an endoscopic optical system, which is provided separate from an operating-microscopic optical system, into an eyepiece optical system of the operating microscope so that an image from the operating-microscopic optical system and the image from the endoscopic optical system are simultaneously observed;

wherein said image projecting optical system comprises a collimating optical system, which collimates a beam of rays emergent from the image derived from the endoscopic optical system;

an imaging optical system, which forms an image on an image surface of the operating-microscopic optical system provided for observation via an eyepiece using said beam of parallel rays emergent from said collimating optical system; and wherein said imaging optical system is constructed to be movable in such a range as allows an entrance aperture thereof to receive said beam of parallel rays.

2. An operating microscope according to claim 1, wherein an optical axis of said imaging optical system aligned with said beam of parallel rays is parallel to a direction in which said eyepiece optical system moves for adjustment of an interpupillary distance, and said imaging optical system is further constructed to be movable along the optical axis in such a range as allows an entrance aperture thereof to receive said beam of parallel rays.

3. An operating microscope according to claim 1, wherein an optical axis of said imaging optical system aligned with said beam of parallel rays is perpendicular to a direction in which said eyepiece optical system moves for adjustment of interpupillary distance, and said imaging optical system is further constructed to be movable in a plane perpendicular to said beam of parallel rays in such a range as allows an entrance aperture thereof to receive said beam of parallel rays.

4. An operating microscope according to any one of claims 1, 2 or 3, wherein one part of optical elements constituting said imaging optical system is constructed to be a light intercepting member for eclipsing a portion of the image obtained by the operating-microscopic optical system, and the image from the endoscopic optical system is projected on the eclipsed portion.

5. An operating microscope according to any one of claims 1, 2 or 3, wherein one part of optical elements constituting said imaging optical system is constructed to be a movable member, such that an observer may shift the image derived form the endoscopic optical system out of an observation field formed by said eyepiece optical system by displacing said movable member.

6. An operating microscope according to any one of claims 1, 2 or 3, wherein an exit pupil of said image projecting optical system is formed via said eyepiece optical system at the same position as an exit pupil of the operating-microscopic optical system and has a diameter larger than that of said exit pupil of the operating-microscopic optical system.

7. An operating microscope according to any one of claims 1, 2 or 3, wherein:

a binocular optical system inclusive of said eyepiece optical system, at least one electronic image display device constructed and arranged to display the image from the endoscopic optical system, and at least one image projecting optical system for projecting a beam of rays emergent from said electronic image display means onto the image surface are housed in a binocular housing to form a unit, said unit being removably mounted on a main housing of the operating microscope.

8. An operating microscope according to any one of claims 1, 2 or 3, wherein at least one electronic image display device constructed and arranged to display the image from the endoscopic optical system and at least one image projecting optical system for projecting a beam of rays emergent from said electronic image display means onto the image surface are housed in a housing to form a unit, said unit being removably mounted on a binocular housing of the operating microscope.

9. An operating microscope according to any one of claims 1, 2, or 3, wherein a binocular section of the operating microscope comprises a movable housing and a fixed housing wherein the binocular section has variable inclination angle, such that said movable housing housing, at least one electronic image display device constructed and arranged to display the image from the endoscopic optical system and at least one image projecting optical system for projecting a beam of rays emergent from said electronic image display device onto the image surface.

10. An operating microscope according to any one of claims 1, 2 or 3, wherein an LCD is used for displaying the image from the endoscopic optical system, and said image projecting optical system satisfies the condition:

$$A \geq (H/\tan 7°)$$

wherein A is a distance from a display surface of said LCD to an entrance pupil of said image projecting optical system, and H is a distance from a center point to a periphery of the image from the endoscopic optical system as displayed on the display surface of said LCD.

11. An operating microscope according to any one of claims 1, 2 or 3, further comprising a binocular housing that is provided with a space of a predetermined size at a position to face a forehead of an observer, at least one electronic image display device constructed and arranged to display an image derived from an image pickup optical system, and at least one image projecting optical system arranged inside said space.

12. An operating microscope according to claim 2 or 3, further comprising at least one electronic image display device, a display section of said electronic image display device being divided by an image processing device into at least two subsections to display the image from the endoscopic optical system and another electronic image simultaneously, and said images displayed on said electronic image display device being projected onto the image surface of the operating-microscopic optical system by said image projecting optical system.

13. An operating microscope according to claims 2 or 3, further omprising at least one electronic image display device, a display section of said electronic image display device being divided by an image processing means into at least two subsections to display the image from the endoscopic optical system and another electronic image simultaneously, and said images displayed on said electronic image display device being projected onto the image surface of the operating-microscopic optical system by said image projecting optical system, said image projecting system further comprising a half mirror and a full mirror, the half mirror projecting a part and the full mirror projecting another part of the images being projected.

14. An operating microscope. comprising:

an image projecting optical system for introducing an image derived from an image pickup optical system, which is provided separate from an operating-microscope optical system, into an eyepiece optical system of the operating microscope so that an image from the operating-microscopic optical system and the image from said image pickup optical system are simultaneously observed;

wherein said image projecting optical system includes a collimating optical system, which collimates a beam of rays emergent from the image derived from the image pickup optical system, and an imaging optical system, which forms an image on an image surface of the operating-microscopic optical system provided for observation via an eyepiece using said beam of parallel rays emergent from said collimating optical system; and wherein said imaging optical system is constructed to be movable in such a range as allows an entrance aperture thereof to receive said beam of parallel rays.

15. An operating microscope, comprising:

an image projecting optical system for introducing an electronic image into an eyepiece optical system of the operating microscope so that an image from the operating-microscopic optical system and the image from the image pickup optical system are simultaneously observed;

wherein said image projecting optical system includes a collimating optical system, which collimates a beam of rays emergent from the image derived from the endoscopic optical system, and an imaging optical system, which forms an image on an image surface of the operating-microscopic optical system provided for observation via an eyepiece using said beam of parallel rays emergent from said collimating optical system; and wherein said imaging optical system is constructed to be movable in such a range as allows an entrance aperture thereof to receive said beam of parallel rays.

* * * * *

UNITED STATES PATENT AND TRADEMARK OFFICE
CERTIFICATE OF CORRECTION

PATENT NO. : 6,088,154
DATED : July 11, 2000
INVENTOR(S) : MORITA

It is certified that error appears in the above-identified patent and that said Letters Patent is hereby corrected as shown below:

amend claim 15 as follows:

15. An operating microscope comprising:
    an image projecting optical system for introducing an electronic image into an eyepiece optical system of the operating microscope so that an image from the operating-microscopic optical system and [the image from the image pickup optical system] said electronic image are simultaneously observed;
    wherein said image projecting optical system includes a collimating optical system, which collimates a beam of rays emergent from [the image derived from the endoscopic optical system] said electronic image, and
    an imaging optical system, which forms an image on an image surface of the operating-microscopic optical system provided for observation via eyepiece using said beam of parallel rays emergent from said collimating optical system; and
    wherein said imaging optical system is constructed to be movable in such a range as allows an entrance aperture thereof to receive said beam of parallel rays.

Signed and Sealed this

First Day of May, 2001

Attest:

NICHOLAS P. GODICI

*Attesting Officer*     *Acting Director of the United States Patent and Trademark Office*